(12) United States Patent
Flaherty et al.

(10) Patent No.: US 6,283,951 B1
(45) Date of Patent: Sep. 4, 2001

(54) SYSTEMS AND METHODS FOR DELIVERING DRUGS TO SELECTED LOCATIONS WITHIN THE BODY

(75) Inventors: J. Christopher Flaherty; Joshua Makower, both of Los Altos; Philip C. Evard, Palo Alto; Patrick E. MacAulay, San Jose; Jason B. Whitt, San Francisco; Robert C. Colloton; K. Angela Macfarlane, both of Cupertino, all of CA (US)

(73) Assignee: Transvascular, Inc., Menlo Park, CA (US)

( * ) Notice: Subject to any disclaimer, the term of this patent is extended or adjusted under 35 U.S.C. 154(b) by 0 days.

(21) Appl. No.: 09/048,147

(22) Filed: Mar. 25, 1998

Related U.S. Application Data

(63) Continuation-in-part of application No. 08/730,327, filed on Oct. 11, 1996, and a continuation-in-part of application No. 08/730,496, filed on Oct. 11, 1996.

(51) Int. Cl.⁷ ................................................. A61M 25/098
(52) U.S. Cl. ................ 604/529; 604/164.11; 604/164.13
(58) Field of Search ............................... 604/20, 21, 187, 604/198, 174, 264, 272, 523, 528, 529, 103.01, 103.02, 164.01, 164.1, 164.11, 164.13, 165.04, 96.01

(56) References Cited

U.S. PATENT DOCUMENTS 3,516,408  6/1970  Montanti .
4,291,013  9/1981  Wahlig et al. ......................... 424/16

(List continued on next page.)

FOREIGN PATENT DOCUMENTS 553259  10/1991  (EP) ............................. A61M/25/01
511499  3/1992  (EP) ............................. A61M/25/00

(List continued on next page.)

OTHER PUBLICATIONS

PCT International Publication, WO 97/13471, Joshua Makower, "A Device, System and Method for Interstitial Transvascular Intervention", Apr. 17, 1997.

(List continued on next page.)

Primary Examiner—Anhtuan T. Nguyen
Assistant Examiner—Jeremy Thissell
(74) Attorney, Agent, or Firm—Lyon & Lyon LLP

(57) ABSTRACT

A transvascular system for delivering a drug to a tissue region from a blood vessel, such as a coronary vein, includes a catheter having a distal portion with puncturing, orientation, drug delivery, and imaging elements. The puncturing element is deployable for penetrating the vessel wall to access the tissue region. The orientation element, e.g. a "cage" including a plurality of struts and/or a radiopaque marker, has a predetermined relationship with the puncturing element, the imaging element detecting the location of the orientation element with respect to the tissue region to orient the puncturing element. The catheter is percutaneously introducing into the vessel, the puncturing element is oriented towards the tissue region, the puncturing element is deployed to access the tissue region, and the drug is delivered to the tissue region. An ablation device may also be deployed to create a cavity in the tissue region for receiving the drug therein, or an indwelling catheter may be advanced into and left in the tissue region. An implantable reservoir device is also disclosed, including an enclosed membrane on an expandable frame that defines a reservoir and includes a porous region. The reservoir device may be deployed and expanded within a blood vessel, and may be filled in situ or prefilled with a drug that passes through the porous region. Alternatively, a pair of expandable endovascular blockers may be used to isolate a section of a blood vessel which may be filled with a drug that may be absorbed by the surrounding tissue.

41 Claims, 13 Drawing Sheets

U.S. PATENT DOCUMENTS

| | | | |
|---|---|---|---|
| 4,576,604 | 3/1986 | Guittard et al. | 604/890 |
| 4,578,061 | 3/1986 | Lemelson | 604/164 |
| 4,774,949 | 10/1988 | Fogarty | 128/348.1 |
| 4,794,931 | 1/1989 | Yock | 128/660.03 |
| 4,859,470 | 8/1989 | Guittard et al. | 424/473 |
| 4,997,431 | 3/1991 | Isner et al. | 606/15 |
| 5,047,039 | 9/1991 | Avant et al. . | |
| 5,054,492 | 10/1991 | Scribner et al. | 128/662.06 |
| 5,106,386 | 4/1992 | Isner et al. | 606/15 |
| 5,167,239 * | 12/1992 | Cohen et al. . | |
| 5,190,528 | 3/1993 | Fonger et al. | 604/171 |
| 5,193,546 | 3/1993 | Shaknovich | 128/662.06 |
| 5,242,397 | 9/1993 | Barath et al. | 604/96 |
| 5,254,089 | 10/1993 | Wang | 604/96 |
| 5,282,810 | 2/1994 | Allen et al. . | |
| 5,287,861 | 2/1994 | Wilk . | |
| 5,304,121 | 4/1994 | Sahatjian | 604/53 |
| 5,312,341 | 5/1994 | Turi . | |
| 5,330,496 | 7/1994 | Alferness | 606/171 |
| 5,336,252 * | 8/1994 | Cohen | 607/119 |
| 5,342,394 | 8/1994 | Mastsuno et al. | 606/213 |
| 5,345,940 | 9/1994 | Seward et al. | 128/662.06 |
| 5,354,279 | 10/1994 | Holfing | 604/164 |
| 5,366,490 | 11/1994 | Edwards et al. | 607/99 |
| 5,373,849 | 12/1994 | Maroney et al. | 128/662.06 |
| 5,397,307 | 3/1995 | Goodin | 604/96 |
| 5,409,019 | 4/1995 | Wilk . | |
| 5,419,777 | 5/1995 | Holfing | 604/264 |
| 5,423,878 | 6/1995 | Franz | 607/122 |
| 5,429,144 | 7/1995 | Wilk . | |
| 5,429,634 | 7/1995 | Narciso, Jr. | 604/890.1 |
| 5,443,497 | 8/1995 | Venbrux . | |
| 5,452,733 | 9/1995 | Sterman et al. . | |
| 5,462,523 | 10/1995 | Samson et al. | 604/30 |
| 5,464,395 | 11/1995 | Faxon et al. | 604/96 |
| 5,499,630 | 3/1996 | Hiki et al. | 128/662.05 |
| 5,507,724 | 4/1996 | Hoffmann et al. | 604/53 |
| 5,523,092 | 6/1996 | Hanson et al. | 424/423 |
| 5,536,250 | 7/1996 | Klein et al. | 604/96 |
| 5,538,504 | 7/1996 | Linden et al. | 604/53 |
| 5,551,954 | 9/1996 | Buscemi et al. | 623/1 |
| 5,554,114 | 9/1996 | Wallace et al. | 604/53 |
| 5,554,182 | 9/1996 | Dinh et al. | 623/1 |
| 5,569,197 | 10/1996 | Helmus et al. | 604/96 |
| 5,570,693 | 11/1996 | Jang et al. | 128/662.06 |
| 5,571,086 | 11/1996 | Kaplan et al. | 604/96 |
| 5,571,151 | 11/1996 | Gregory | 607/88 |
| 5,588,432 * | 12/1996 | Crowley | 128/660.03 |
| 5,588,960 | 12/1996 | Edwards et al. | 604/20 |
| 5,596,990 * | 1/1997 | Yock et al. | 128/662.06 |
| 5,597,378 | 1/1997 | Jervis | 606/78 |
| 5,599,300 | 2/1997 | Weaver et al. | 604/54 |
| 5,607,418 | 3/1997 | Arzbaecher | 604/891.1 |
| 5,609,574 | 3/1997 | Kaplan et al. | 604/53 |
| 5,614,204 | 3/1997 | Cochrum | 424/423 |
| 5,628,784 | 5/1997 | Strecker | 623/1 |
| 5,634,895 | 6/1997 | Igo et al. | 604/21 |
| 5,661,133 | 8/1997 | Leiden et al. | 514/44 |
| 5,662,609 | 9/1997 | Slepian | 604/101 |
| 5,665,077 | 9/1997 | Rosen et al. | 604/266 |
| 5,674,198 | 10/1997 | Leone | 604/101 |
| 5,693,029 | 12/1997 | Leonhart | 604/264 |
| 5,704,361 | 1/1998 | Seward et al. | 128/662.06 |
| 5,704,926 | 1/1998 | Sutton | 604/282 |
| 5,713,363 | 2/1998 | Seward et al. | 128/662.06 |
| 5,713,853 | 2/1998 | Clark et al. | 604/53 |
| 5,713,887 | 2/1998 | Mills et al. | 604/890.1 |
| 5,724,975 | 3/1998 | Negus et al. | 128/661.09 |
| 5,724,977 | 3/1998 | Yock et al. | 128/662.06 |
| 5,728,123 | 3/1998 | Lemelson et al. | 604/22 |
| 5,735,847 | 4/1998 | Gough et al. | 606/41 |
| 5,738,658 | 4/1998 | Maus et al. | 604/151 |
| 5,771,895 | 6/1998 | Slager | 128/662.06 |
| 5,772,629 | 6/1998 | Kaplan | 604/52 |
| 5,772,632 | 6/1999 | Forman | 604/101 |
| 5,807,306 * | 9/1998 | Shapland et al. | 604/21 |
| 6,004,269 * | 12/1999 | Crowley et al. | 600/439 |
| 6,053,911 * | 4/2000 | Ryan et al. | 606/33 |

FOREIGN PATENT DOCUMENTS

| | | | |
|---|---|---|---|
| 8700632 | 10/1988 | (NE) | A61B/17/36 |
| 9200113 | 1/1992 | (WO) | A61M/5/00 |
| 9210142 | 6/1992 | (WO) | A61B/17/36 |
| 9211890 | 7/1992 | (WO) | A61M/25/00 |
| 9211895 | 7/1992 | (WO) | A61M/31/00 |
| 9325263 | 12/1993 | (WO) | A61M/25/00 |
| 9408653 | 4/1994 | (WO) | A61M/25/00 |
| 9426341 | 11/1994 | (WO) | A61M/25/00 |
| 9501138 | 1/1995 | (WO) | A61F/2/06 |
| 9524235 | 9/1995 | (WO) | A61M/25/00 |
| 9604952 | 2/1996 | (WO) | A61M/29/02 |
| 9635464 | 11/1996 | (WO) | A61M/5/145 |
| 9635469 | 11/1996 | (WO) | A61M/25/00 |
| 9701988 | 1/1997 | (WO) . | |
| 9716170 | 5/1997 | (WO) | A61K/9/00 |
| 9717029 | 5/1997 | (WO) | A61B/17/39 |
| 9718067 | 5/1997 | (WO) | B26F/1/24 |
| 9819614 | 5/1998 | (WO) | A61B/17/36 |
| 9819618 | 5/1998 | (WO) | A61B/19/00 |
| 9838939 | 9/1998 | (WO) | A61B/19/00 |

OTHER PUBLICATIONS

Steven L. Schwartz, M.D., et al., "Real–Time Intracardiac Two–Dimensional Echocardiography: An Experimental Study in In Vivo Feasibility, Imaging Planes, and Echocardiographic Anatomy", Echocardiography: A Jrnl. of CV Ultrasound & Allied Tech. vol. 7(4): 443–455, (1990).

Michael Von Ludinghausen, et al., "Atrial Veins of the Human Heart", Clinical Anatomy 8: 169–189 (1995).

N. Bom, C.J. Slager, F.C. Van Egmond, C.T. Lancee, P.W. Serruys; Intra–Arterial Ultrasonic Imaging for Recanalization; Oct. 26, 1987; pp 41–45.

Severin P. Schwarzacher, MD; Peter J. Fitzgerald MD, PhD; Jonas A. Metz, MD; Alan C. Yeung, MD; Steve N. Oesterle, MD; Martin Belef, MS; Robert S. Kernoff, RS; Pau G. Yock, MD. Enhancement of spatial orientation of intravascular ultrasound images with side holes in guiding catheters; Jun. 98; pp 1063–1066.

K. Sudhir, P.J. Fitzgerald, J.S. MacGregor, T. DeMarco, T.A. Ports, K Chatterjee, P.G. Yock; Transvenous Coronary Ultrasound Imaging; Jul. 91; pp 1957–1961.

K.L. March; Methods of local gene delivery to vascular tissues; 1996; pp 215–223.

J Folkman; Angiogenic Therapy of the Human Heart; 1998; 628–629.

P.G. Yock, D.T. Linker, B.A.J. Angelsen, Dr Tech; Two–Dimensional Intravascular Ultrasound: Technical Development and Initial Clinical Experience; Aug. 1989; 296–304.

Y. Kobayashi, P.G. Yock, P.J. Fitzgerald, perivascular IVUS Landmarks, 1998; pp 35–42.

* cited by examiner

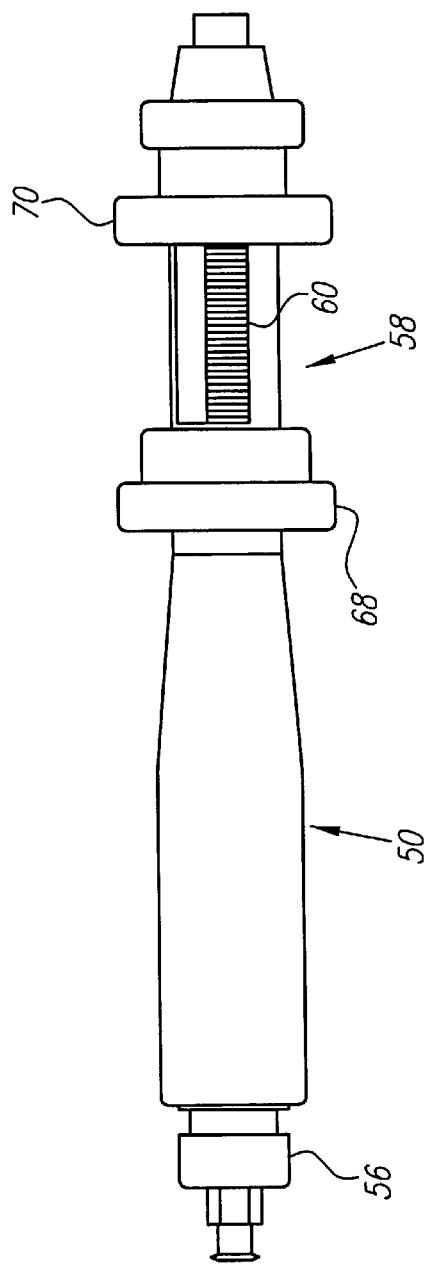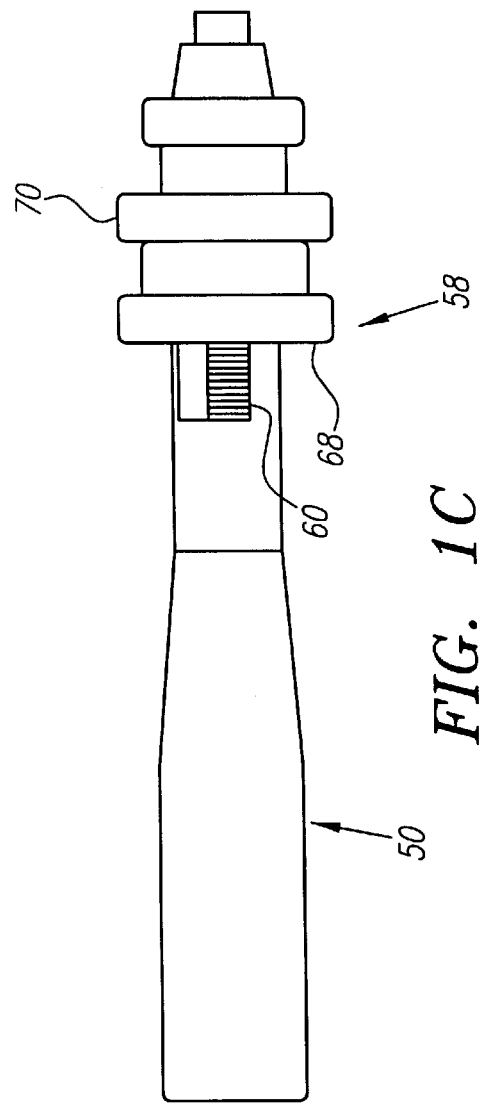

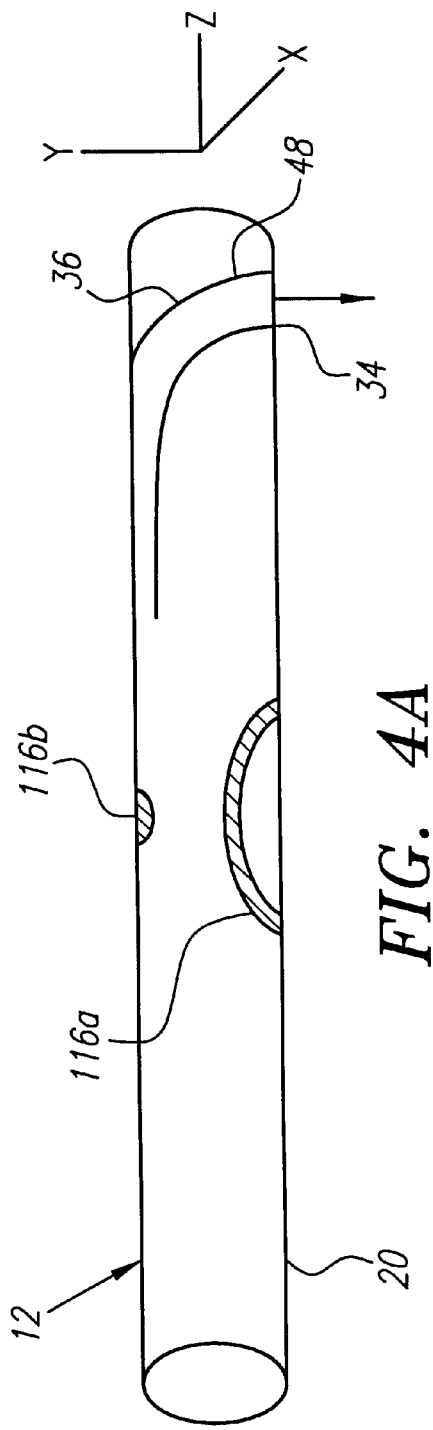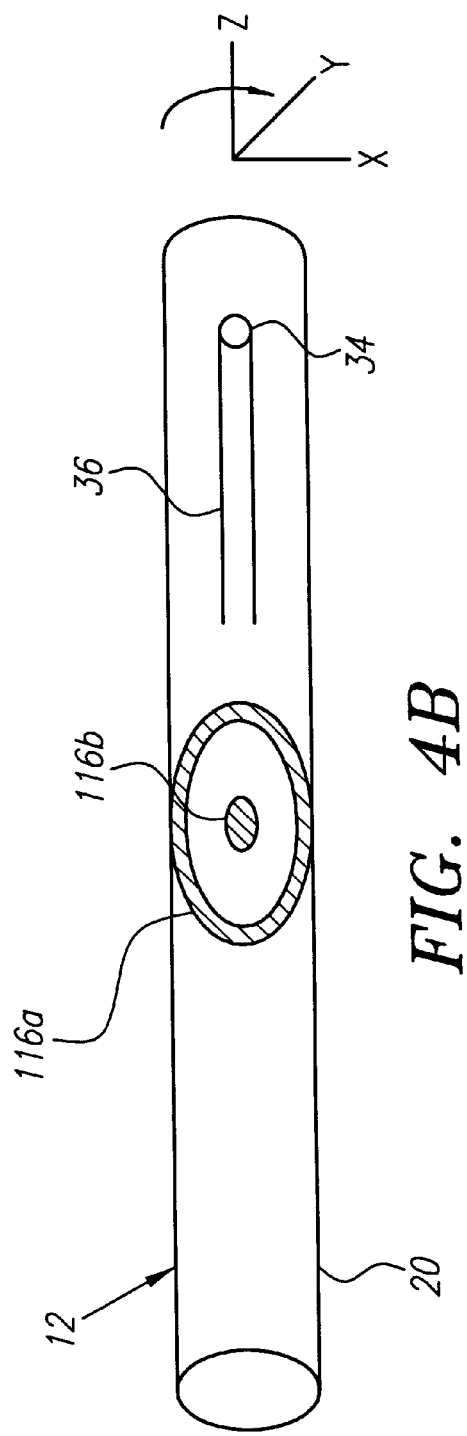
FIG. 4A
FIG. 4B ental delivery of drugs using ionophoresis. A first electrode may be provided within a perfusion balloon, and a second electrode provided on an external region of the patient's body near the artery. When direct current is applied between the electrodes, a drug carried by an electrically charged compound may be directed along the path of current flow from the internal electrode towards the external electrode in an attempt to improve penetration of the drug into the arterial wall and surrounding tissue.

SYSTEMS AND METHODS FOR DELIVERING DRUGS TO SELECTED LOCATIONS WITHIN THE BODY

This application is a continuation-in-part of applications Ser. Nos. 08/730,327 and 08/730,496, both filed Oct. 11, 1996, the disclosures of which are expressly incorporated herein by reference.

FIELD OF THE INVENTION

The present invention relates generally to systems and methods for delivering substances into a body, more particularly to systems and methods that use the cardiovascular system as a conduit to deliver drugs, such as therapeutic drugs, genes, growth factors and the like, directly to selected tissue regions within the body, and most particularly to systems and methods that deliver drugs from the venous system transvascularly to selected remote tissue regions.

BACKGROUND

It is often desirable to deliver drugs into a patient's body to treat medical conditions. In particular, a variety of drug therapies are available for treating the coronary system, either alone or in combination with more invasive procedures. Such therapies may include delivering substances, such as nitroglycerin, epinepharin, or lydocaine, endocardially or into the pericardial space to treat the coronary system. In addition, heparin, hirudin, ReoPro™ or other anti-thrombotic compounds may be infused into blood vessels associated with the coronary system, such as occluded coronary arteries, or elsewhere in the cardiovascular system. More recently, gene therapy, e.g. introducing genetic material, and growth factor therapy, e.g. introducing proteins, cells or vectors including angiogenic growth factors, have been demonstrated to provide potential benefits in treating ischemic heart tissue and other regions of the coronary system, for example, by stimulating growth of neovascular conduits, which may evolve into new blood vessels.

In current medical therapy, one method of delivering such drugs involves percutaneously introducing an infusion catheter into the patient's cardiovascular system. A distal portion of the catheter is directed to a desired endovascular location, for example into a coronary artery, and a drug is infused into the artery at a location reachable intraluminally. The catheter may include a lumen extending between its proximal and distal ends, the distal end having one or more outlet ports. A source of the drug, such as a syringe, may be connected to the proximal end and the drug delivered through the lumen and outlet port(s) into the desired location.

For example, a "bolus," i.e. a relatively large single dose of a drug, may be delivered using an infusion catheter into an artery, which may be absorbed by the arterial wall, the surrounding tissue, and/or may be carried by blood flow to regions further downstream from the delivery location. Alternatively, the drug may be infused continuously or intermittently into the artery for an extended period of time.

The infusion catheter often includes a porous perfusion balloon on its distal end, the interior of which communicates with the outlet port(s) and lumen in the catheter. Pores or holes in the balloon may be arranged to direct the drug from the balloon towards the arterial wall to improve penetration into the arterial wall and attempt to localize delivery. In addition, the infusion catheter may be provided with an electrode and/or a heating element on or in the balloon to cause electroporation or to heat the surrounding tissue to further improve localized delivery.

Some devices try to enhance localized delivery of drugs using ionophoresis. A first electrode may be provided within a perfusion balloon, and a second electrode provided on an external region of the patient's body near the artery. When direct current is applied between the electrodes, a drug carried by an electrically charged compound may be directed along the path of current flow from the internal electrode towards the external electrode in an attempt to improve penetration of the drug into the arterial wall and surrounding tissue.

As an alternative to perfusion balloons and/or infusion catheters, a drug may be embedded in or deposited on a catheter, e.g. in the catheter wall, the wall of a non-porous balloon on the catheter, and/or a coating on the catheter. After the distal end is directed to a desired location, the drug may be delivered into an artery, for example, by ionophoresis similar to that described above or by simply allowing the drug to dissolve within the artery.

In an alternative to delivering a bolus of drugs, it is often desirable to provide sustained delivery of a drug within the cardiovascular system. For example, a pair of occlusion balloons disposed along the length of a catheter may be provided on an infusion catheter that may be directed endovascularly to a desired location within an artery. The balloons may be inflated to isolate a section of the artery between them, and a drug may be delivered into the isolated section in an attempt to provide sustained delivery to the isolated section. The balloons are then deflated, and the catheter removed from the body.

Drug delivery devices may also be implanted within an artery to provide sustained delivery. For example, U.S. Pat. No. 5,628,784 issued to Strecker discloses an expandable annular sleeve that may be deployed within an artery. A small quantity of drugs may be introduced between the sleeve wall and the surrounding arterial wall to directly contact the arterial wall, where they may be absorbed over an extended period of time. PCT Publication No. WO 95/01138 discloses a porous ceramic sleeve that may be implanted directly in tissue, such as in bone marrow or a surgically created pouch. The sleeve includes drugs within a cell culture or matrix in the sleeve, which may, for example, be dispersed in the pores of the sleeve or be provided in a cylindrical insert.

In addition, a number of extravascular methods have also been suggested. For example, drugs may be injected directly into a desired tissue region, typically by accessing the region through a chest incision. Alternatively, a polymer gel or drug-soaked sponge may be attached to the outside of a vessel or to a portion of the endocardium to be absorbed by the contacted region. In addition, the pericardial space may have substances injected directly into it, for example by accessing the pericardial sac through a chest incision. Such methods may provide either single dose or sustained delivery of drugs to the heart.

One of the problems often associated with existing methods is dilution or "wash-out" of the drug during delivery. Dilution may substantially reduce the effectiveness of a therapy by preventing sufficient quantities of the drug from reaching a desired region. For example, during endovascular delivery using an infusion catheter, the drug may be diluted as it travels through the arterial wall or may be carried downstream through the artery to other regions within the coronary system and/or elsewhere in the body.

The volume of drug may be increased to offset dilution concerns, but this may exacerbate concerns about undesired dissemination of the drug. For example, certain therapeutic drugs, genetic material and growth factors may have undesired global side effects. Releasing a drug into the blood stream may allow it to be carried throughout the coronary system or elsewhere in the body where it may have significant adverse effects. Similar adverse effects may result from pericardial delivery, in which a drug may be absorbed throughout the coronary system, rather than only in a desired local region.

Further, many conventional methods are unable to provide effective sustained delivery, which may be important to the success of certain treatments, such as gene or growth factor therapy, where it may be desirable to maintain a drug in a desired region for hours, days or even longer. Occlusion systems, such as the dual occlusion balloon catheter, or the implantable sleeves described above, may be able to isolate a region of an artery for some sustained treatments.

Such occlusion devices, however, may introduce additional risks associated with obstructing flow within the coronary system for extended periods of time. In particular, if the arterial system is occluded for more than short periods of time during treatment, substantial damage may occur, for example, ischemia and possibly infarction of tissue downstream from the occluded region.

Conventional endovascular systems may also be inadequate to access certain tissues in need of treatment. For example, infusion catheters may be unable to pass through an occluded region of an artery to treat ischemic tissue downstream of the region. Further, it may be hazardous to direct an endovascular device through a stenotic region because of the risk of releasing embolic material from the arterial wall, which may travel downstream and become embedded in other vessels or even travel to vital organs, such as the brain, where they may cause substantial damage or even death.

More invasive methods, such as direct injection of drugs, may provide access to otherwise unattainable regions. Such methods, however, typically involve open-chest or other invasive surgical procedures, and the costs and risks associated with them.

Accordingly, there is a need for improved systems and methods of delivering drugs to desired locations within the body with greater precision, reduced global side-effects, and/or that substantially reduce the problems of the previous systems and methods.

SUMMARY OF THE INVENTION

The present invention is directed to systems and methods for delivering a drug to a tissue region within a patient's body, and in particular to systems and methods that use the venous system as a conduit to deliver a drug directly to a remote tissue region, or to facilitate a catheter-based intervention. "Drug" as defined herein includes any therapeutic drugs, genetic materials, growth factors, cells, e.g. myocites, vectors carrying growth factors, and similar therapeutic agents or substances that may be delivered within a patient's body for any therapeutic, diagnostic or other procedure. In one aspect of the present invention, a transvascular catheter system is provided that generally includes a catheter, a drug delivery element, an orientation element, and possibly a puncturing element and/or an imaging element. The catheter has a proximal portion and a distal portion adapted for insertion into a blood vessel, and defines a periphery and a longitudinal axis. The puncturing element is deployable from the distal portion in a predetermined relationship with the circumference or periphery of the catheter, and includes a distal tip adapted to penetrate a wall of a blood vessel to access a tissue region beyond the wall of the blood vessel. The drug delivery element is provided on the distal portion for delivering a drug to the tissue region, and an orientation element is also provided on the distal portion in a predetermined relationship with the periphery of the catheter and the puncturing element.

Preferably, the catheter has a peripheral opening at a predetermined location on the periphery of the distal portion through which the puncturing element may be deployed, and a needle lumen communicating with the peripheral opening for receiving the puncturing element therethrough. The needle lumen includes a deflecting element adapted to direct the distal tip substantially transversely with respect to the longitudinal axis when the puncturing element is deployed.

The system may include an imaging element adjacent the orientation element for detecting the location of the orientation element with respect to the tissue region. For example, the imaging element may be an ultrasound transducer which may be received in a lumen extending between the proximal and distal portions of the catheter.

In a first preferred embodiment, the puncturing element is a needle and the drug delivery element is a lumen in the needle. The needle may include an array of outlet ports for providing a predetermined flow pattern of fluid into the tissue region accessed by the needle. In addition, at least a portion of the needle may be a conductive material electrically coupled to a proximal end of the puncturing element for coupling the needle to a source of electric current. Alternatively, the puncturing element may be a plurality of needles deployable from predetermined locations on the distal portion to provide a selected trajectory pattern into the tissue region.

In a second preferred embodiment, the puncturing element includes a guide wire, and the drug delivery element is deployable over the guide wire. For example, the drug delivery element may be an infusion catheter, possibly including a perfusion balloon. Alternatively, the drug delivery element may include an indwelling catheter which is delivered over the guide wire, either before or after removal of the transvascular catheter. The drug delivery element may include a first electrode thereon adapted to be electrically coupled to a second electrode. When direct current is directed between the first and second electrodes, fluid from the drug delivery element may be ionophoretically directed from the drug delivery element towards the second electrode. Alternatively, the drug delivery element may be an osmotic surface on the transvascular catheter, the infusion catheter or the indwelling catheter.

To assist in orienting the system during use, the orientation element preferably has an asymmetric configuration aligned with the puncturing element, for example with the peripheral opening through which the puncturing element may be deployed. In a first preferred embodiment, the orientation element is a "cage" structure that includes a plurality of struts extending axially along the distal portion. Preferably, a first strut is provided at a location in direct axial alignment with the peripheral opening, and a pair of struts are provided opposite the first strut to "point" towards the peripheral opening. Alternatively, the orientation element may include a marker that may be imaged using an external imaging system, and preferably a pair of markers disposed opposite one another on the periphery, either instead of or preferably in addition to the "cage" structure.

A transvascular catheter system in accordance with the present invention may be used to deliver a drug to a tissue region within a patient's body, such as into the myocardium or a coronary artery from the coronary venous system, in a method which may proceed as follows. The distal portion of the catheter may be percutaneously introducing into a blood vessel, and directed endovascularly to a vessel location adjacent to the tissue region selected for treatment. The puncturing element may be oriented towards the selected tissue region, and deployed to access the tissue region. A drug may then be delivered with the drug delivery element to the tissue region.

Preferably, when the puncturing element is being oriented, the orientation element is imaged, for example with an imaging element adjacent the orientation element. The imaging element is preferably operated to obtain an image of the orientation element in relation to the surrounding tissue, thereby identifying the orientation of the puncturing element because of the predetermined relationship between the orientation element and the puncturing element. Preferably, the imaging element is an ultrasound transducer within the catheter that may be used to obtain image slices along a plane substantially normal to the longitudinal axis of the catheter, the images preferably including the orientation element, the selected tissue region and/or other landmarks within the vessel or the surrounding tissue.

Where the puncturing element is a drug delivery needle, the needle may be deployed, penetrating a wall of the blood vessel and entering the tissue region, and the drug may be delivered through a lumen in the needle. Alternatively, a drug delivery element may be deployed in combination with the puncturing element. For example, an infusion catheter may be advanced over the puncturing element to the tissue region, and the drug infused therethrough, or through a porous balloon on the infusion catheter which may be inflated within the tissue region.

Prior to delivering the drug, a "mapping" procedure may be used to ensure that the drug will be delivered as desired into the specific tissue region selected for treatment. For example, a radiographic agent may be delivered using the drug delivery element to observe the flow thereof with respect to the selected tissue region. Once it has been confirmed that the radiographic agent flows as desired into the selected tissue region, the drug may then be introduced, thereby possibly avoiding misdelivery of what are often quite expensive drugs. Alternatively, a radiographic agent and the like may be mixed with the drug to track the flow of the drug within the body, particularly with respect to the selected tissue region.

In another preferred method, the transvascular catheter system may be used to create a drug reservoir directly in a selected tissue region. For example, a tissue ablation device may be provided that is deployable in combination with the puncturing element for creating a cavity in an extravascular tissue region. The ablation device may be advanced over the puncturing element into the tissue region, and an ablation element thereon activated to create a cavity or drug reservoir within the tissue region. A drug may then be introduced into the drug reservoir, which may be sealed from the vessel, for example by introducing a sealant or matrix into the drug reservoir. Alternatively, the drug reservoir may be formed by removing a portion of the tissue region, for example with a cutting instrument or similar mechanical device.

In a further alternative, the transvascular system may be used to facilitate an indwelling catheter-based intervention. The catheter may be introduced into a vessel, and then the puncturing element may be oriented and deployed into a tissue region, such as interstitial tissue or another blood vessel. A guide wire may be advanced into the tissue region, and the transvascular catheter may then be removed, leaving the guide wire in place, possibly anchored to the tissue region. A thin, floppy catheter may be tracked over the guide wire into the tissue region, and left in place within the tissue region, and the wire may be removed. The indwelling catheter may be taped, ported or otherwise secured to the patient depending upon the length of time therapy is desired. The tissue region may then be accessed via the indwelling catheter to deliver a drug to the tissue region as often as desired.

In another aspect of the present invention, an implantable drug reservoir system may be used to provide sustained delivery of a drug within the cardiovascular system of a patient. Generally, the system includes a reservoir device having an expandable frame and a flexible membrane thereon. The frame is adapted to expand between a collapsed condition for insertion into a blood vessel and an enlarged condition for engaging a wall of the blood vessel. The frame is preferably biased towards the enlarged condition, and also preferably defines a longitudinal axis and a periphery.

The flexible membrane is attached to the frame to define a reservoir therein, and includes a porous region, such as a semi-permeable material, that is preferably disposed along the periphery of the frame. A drug, possibly together with an anti-coagulant, is provided within the reservoir that is adapted to pass through the porous region of the membrane. An end region of the membrane may be penetrable, for example by a needle, to facilitate in situ filling of the reservoir.

In an alternative embodiment of the implantable drug reservoir system, a reservoir device similar to that described above may be provided with a septum dividing the reservoir within the membrane into first and second reservoir regions. The membrane preferably includes an osmotic region communicating with the first reservoir region, and the porous region of the membrane preferably communicates with the second reservoir region.

During use, the reservoir device may be introduced along a blood vessel to a location adjacent a selected tissue region, for example within a coronary vein adjacent to an occluded artery or ischemic myocardial tissue. The reservoir device may be deployed and expanded, preferably automatically, to its enlarged condition to anchor the reservoir device within the blood vessel. A drug may be prefilled within the reservoir or an injection device may be advanced to penetrate the membrane of the reservoir device and fill the reservoir in situ with the drug.

The drug may then permeate, seep, or otherwise pass through the porous region, preferably directly into the wall of the vessel and the surrounding tissue region. If desired, the reservoir may be refilled in situ using an injection device as the drug is dispersed or otherwise absorbed by the tissue. Similarly, a reservoir device having a septum panel may deliver the drug in the second reservoir region to the tissue region as the first reservoir region osmotically fills, thereby slowly forcing or "pumping" the drug through the porous region.

In another preferred embodiment of an implantable drug reservoir system, a pair of expandable devices, similar to the reservoir devices may be used. The expandable devices, or endovascular "blockers," include an expandable frame, and a non-porous membrane covering at least one end of the frame, and preferably extending along at least a portion of the periphery.

The first blocker is advanced in a collapsed condition along the blood vessel to a location adjacent the selected tissue region. The first blocker is then expanded to its enlarged condition, thereby sealing the blood vessel at the location from fluid flow along the blood vessel. The second blocker is then advanced in a collapsed condition along the blood vessel to the location, preferably adjacent the first blocker. The second blocker is then expanded to its enlarged condition, thereby further sealing the blood vessel at the location from fluid flow along the blood vessel. The second blocker is preferably deployed a predetermined distance from the first blocker, thereby defining a substantially sealed drug reservoir within the blood vessel itself between the blockers.

A drug may be introduced into the blood vessel adjacent the first blocker, either before or after the second blocker is deployed. For example, the second blocker may include an end panel only on the end away from the drug reservoir between the blockers, and an injection device may be advanced to penetrate the end panel. The drug may then be introduced into the second blocker and consequently into the drug reservoir between the blockers. Thus, a section of a blood vessel may be isolated and a drug delivered therein to provide sustained and localized delivery of the drug into the selected tissue region surrounding the vessel.

Accordingly, a principal object of the present invention is to provide a system and method for precisely delivering a drug to a selected tissue location within the body.

It is also an object to provide a system and method for providing sustained delivery of a drug to a desired location within the body over an extended period of time.

It is also an object to provide a system and method for creating a reservoir within the body for receiving a drug to provide sustained delivery to a desired tissue region within the body.

It is also an object to provide a system and method that use the cardiovascular system as a conduit to deliver a drug to a selected remote tissue region within the body with substantial precision.

It is also an object to provide a system and method for delivering a drug transvascularly using the venous system as a conduit to access a selected remote tissue region.

More particularly, it is specifically an object of the present invention to use the coronary venous system to provide access to a highly remote tissue region of the body, e.g. heart tissue.

Other objects and features of the present invention will become apparent from consideration of the following description taken in conjunction with the accompanying drawings.

BRIEF DESCRIPTION OF THE DRAWINGS

FIGS. 1B and 1C are side views of a handle on the catheter for the transvascular catheter system of FIG. 1A.

FIG. 4 is a side view detail of a catheter, showing a preferred embodiment of an externally detectable orientation element in accordance with the present invention.

DETAILED DESCRIPTION OF THE PREFERRED EMBODIMENTS

Figure 1A:
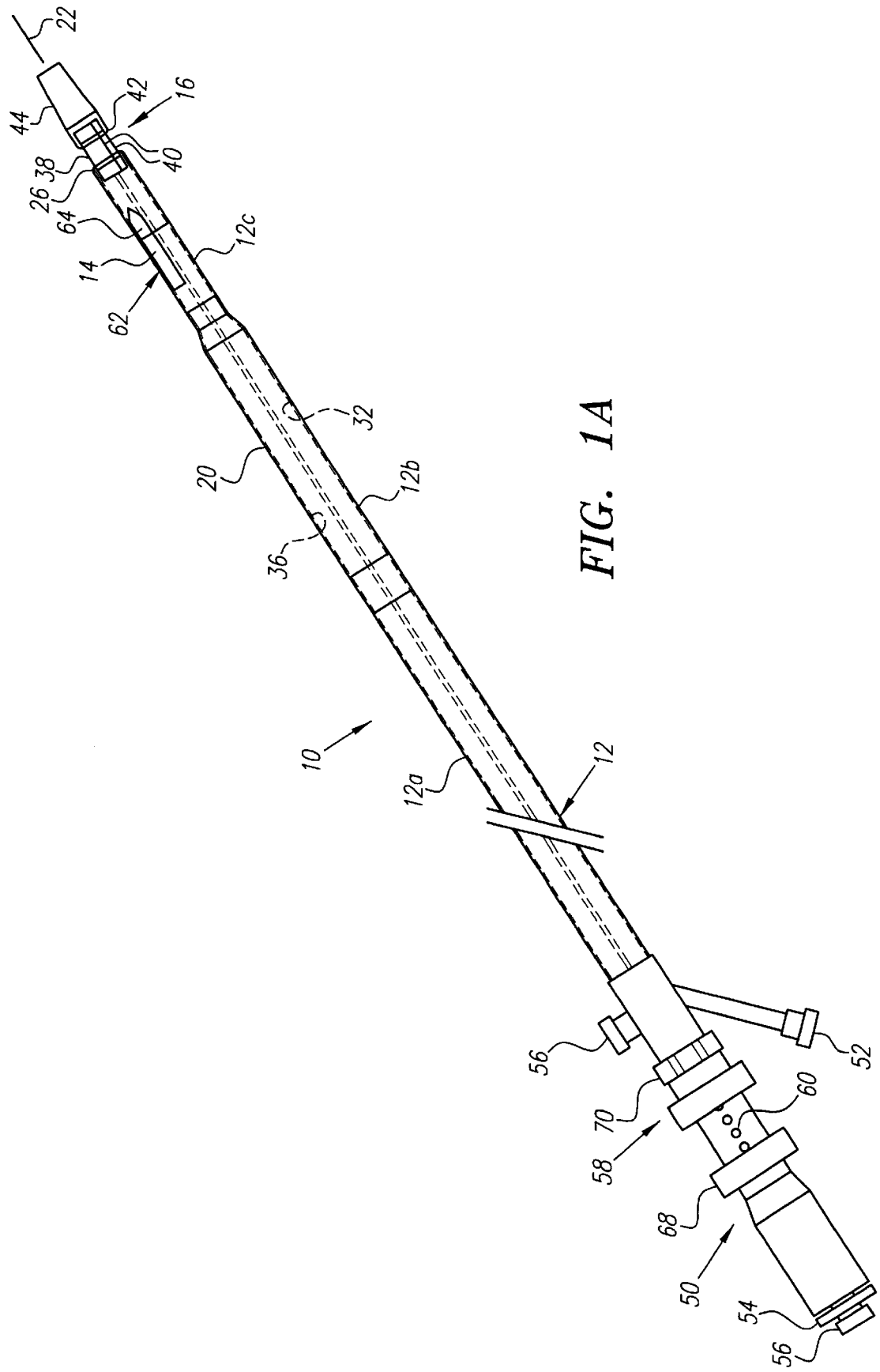
FIG. 1A is a cross-sectional view of a transvascular catheter system in accordance with one aspect of the present invention.
Figure 1D:
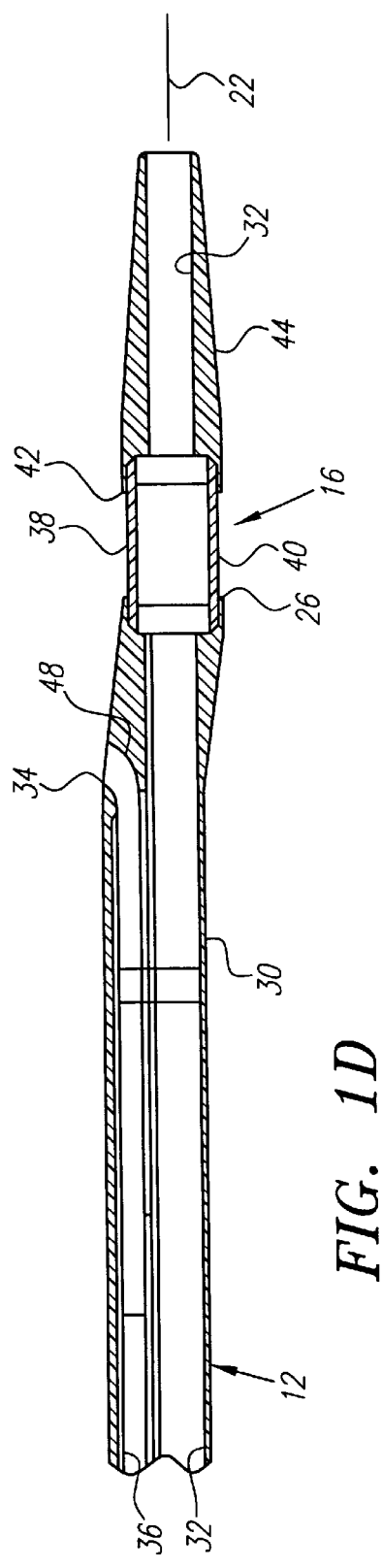
FIG. 1D is a cross-sectional view of the distal portion of a catheter for the transvascular catheter system of FIG. 1A.
Figure 1E:
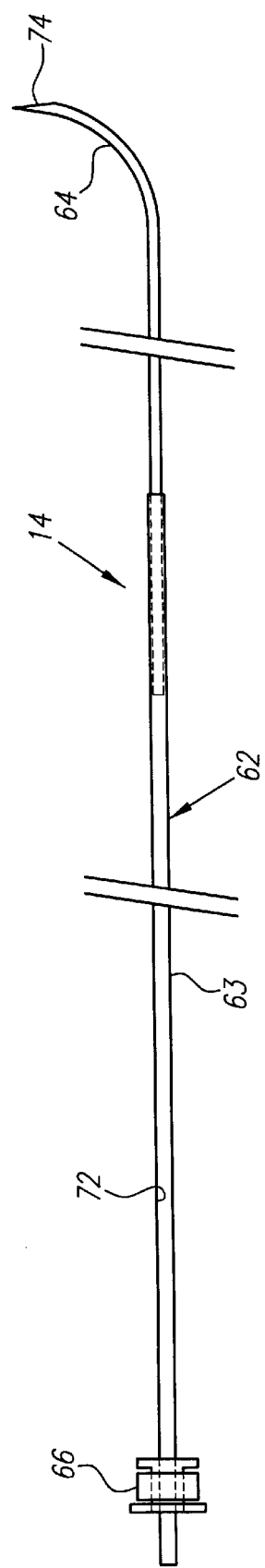
FIG. 1E is a side view of a needle assembly for the transvascular catheter system of FIG. 1A.

Turning now to the drawings, FIGS. 1A–1E and 2 show a preferred embodiment of a transvascular catheter system 10 in accordance with the present invention for delivering a drug to a selected remote tissue region within a body from a blood vessel near the tissue region. The system 10 generally includes a catheter 12, a puncturing element 14, an orientation element (e.g. a "cage" structure 16 described below), and an imaging element 18.

The catheter 12 may be an elongate member having substantially flexible and/or semi-rigid sections, and defining a circumference or periphery 20 and a longitudinal axis 22 between proximal and distal ends 24, 26. The catheter 12 includes a proximal portion 28 having a handle 50 and a distal portion 30 having a size and shape to facilitate insertion into a blood vessel.

An IVUS lumen 32 extends through the catheter 12 from an IVUS entry port 52 in the handle 50 to a tip member 44 on the distal portion 30 for receiving the imaging element 18. A needle lumen 36 also extends from a needle entry port 54 in the handle 50 to a peripheral opening 34 in the distal portion 30 for receiving the puncturing element 14. The needle lumen 36 includes a deflecting element or ramp 48 adjacent the peripheral opening 34.

The catheter 12 may include an extruded dual lumen catheter encapsulated within an outer jacket (not shown), and/or may have a proximal portion that is substantially more rigid than a distal portion. For example, in the preferred embodiment shown in FIG. 1A, the catheter 12 includes a proximal portion 12a, an intermediate portion 12b, and a distal portion 12c, each having a dual lumen catheter segment and an outer jacket segment. The rigidity or Durometer of the dual lumen catheter and outer jacket segments of the proximal portion 12a is preferably 63 and 70, while the remaining segments preferably have a Durometer of 40. Additional information on the construction of the catheter 12, e.g. its material composition, its size and shape, may be found in co-pending applications Ser. Nos.08/730, 327 and 08/730,496, both filed on Oct. 11, 1996, and in PCT Application No. PCT/US97/01459, filed on Jan. 31, 1997, the disclosures of which are expressly incorporated herein by reference.

The orientation element is preferably a marker "cage" structure 16 including a plurality of elongate members or struts 38, 40 on the distal portion 30 located distally of the peripheral opening 34. The struts 38, 40 preferably extend distally from the distal end 26 substantially parallel to the longitudinal axis 22 to the proximal edge 42 of the tip member 44, thereby further defining the IVUS lumen 36. The struts 38, 40 preferably define a peripheral window 46, which may be covered by a material substantially transparent to the imaging element 18 or may remain open to blood flow. The struts 38, 40 are preferably substantially rigid tubular members, such as hypotubes, which are reflective to the imaging element 18, i.e. will produce a reflection or artifact when the imaging element 18 is operated, and/or may be substantially opaque to an external imaging apparatus (not shown).

Preferably, the struts 38, 40 have an asymmetrical configuration about the periphery 20 that has a predetermined relationship with the location of the peripheral opening 34. More preferably, a first strut 38 is located on the periphery 20 directly distally from the location of the peripheral opening 34. A pair of struts 40 are then positioned opposite the first strut 38, thereby defining an isosceles triangle or TRI-POINT™ cross-sectional configuration, with the first bar 38 at the top of the triangle. Thus, the orientation element 16 may "point" circumferentially towards the location of the peripheral opening 34 on the periphery 20, i.e. towards the location from which the puncturing element 14 may be deployed, as described further below.

In an alternative embodiment shown in FIGS. 4A and 4B, the orientation element may include one or more externally visible markers 116 placed at one or more predetermined locations on the periphery 20 of the catheter 12. The markers 116 define a pattern to facilitate detection of the orientation of the distal portion 30 about the longitudinal axis 22 with the aid of an external imaging apparatus. For example, the markers 116 may be formed from a radiopaque material visible using a fluoroscopic imaging system. Preferably, a pair of fluoroscopic markers 116a, 116b are provided on the periphery 20 that uniquely indicate the rotational orientation of the peripheral opening 34, such as the "bulls-eye" arrangement shown. Further discussion of such markers may be found in U.S. Pat. Ser No. 08/730,327 filed Oct. 11, 1996, the disclosure of which is expressly incorporated herein by reference. Although the transvascular catheter system 10 may include both internal and external markers 16, 116 on the catheter 12, preferably only one marker or orientation element is necessary to effectively orient the puncturing element 14.

Returning to FIGS. 1A–1E and 2, the tip member 44 attached to the struts 38, 40 has an annular shape formed from a substantially flexible material to further define the IVUS lumen 32. The tip member 44 is preferably tapered to facilitate insertion into and direction along the lumen of a blood vessel, and is substantially coaxial with the IVUS lumen 32 in the catheter 12 to facilitate the introduction of a guide wire or other instrument axially therethrough.

With particular reference to FIGS. 1A–1C, the handle 50 is preferably a substantially rigid member including the IVUS entry port 52, the needle entry port 54, and a needle lumen flush port 58 in communication with the needle lumen 36. The ports 52, 54 and 58 may include one or more seals to prevent backflow, as will be appreciated by those skilled in the art. A control and/or locking mechanism 58 is located on the handle 50 that includes a needle thumb slide 68 and an adjustable needle stop 70 that cooperatively slide along a graduated region 60 of the handle 50.

The needle thumb slide 68 may be directed axially along the graduated region 60 to deploy the puncturing element 14, as described more particularly below. The adjustable needle stop 70 is slidable on the handle 50 and is securable at a plurality of positions on the graduated region 60 of the handle 50. Thus, the adjustable needle stop 70 may be locked at a first position on the graduated region 60, loosened, directed axially to a second position on the graduated region 60, and locked at the second position to limit the movement of the needle thumb slide 68, and consequently the depth of penetration of the puncturing element 14.

Turning to FIGS. 1A–1E, the puncturing element 14 is preferably a needle assembly 62 including an elongate tubular body 63 having a puncturing distal tip 64 and a proximal safety clip 66. The needle assembly 62 and/or the distal tip 64 are preferably formed from a shape memory alloy, such as Nitinol, that is precurved to enhance transverse deployment of the distal tip 64. The distal tip 64 may be inserted into the needle entry port 54 and directed distally through the needle lumen 36 until the safety clip 66 abuts the needle thumb slide 68 on the handle 50. The needle thumb slide 68 then may be secured to the needle assembly 62, for example with ball detents that extend radially into the needle lumen 36 from the needle thumb slide 68 (not shown), for controlling axial movement of the needle assembly 62.

Figure 5A:
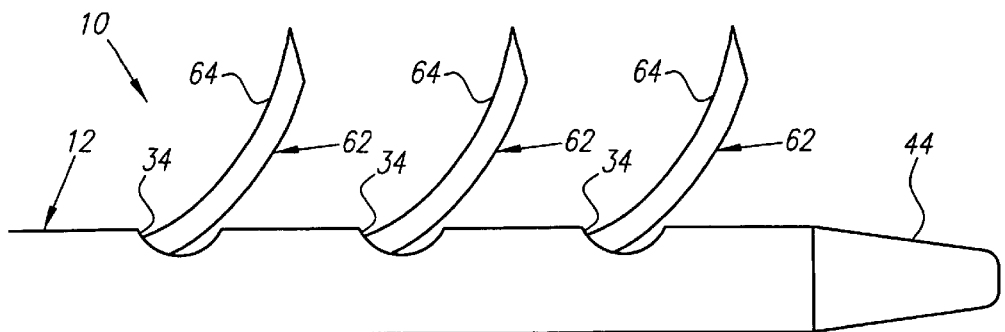
FIG. 5A is a side view of an alternative embodiment of the distal portion, including a plurality of needle assemblies.

Preferably, the needle assembly 62 includes a drug delivery lumen 72 extending from the safety clip 66 to an outlet 74 in the distal tip 64. The outlet 74 may be a single opening for directing fluid distally beyond the distal tip 64, or may include a plurality of openings having a predetermined outlet pattern. For example, as shown in FIG. 5C, the distal tip 64 may include a closed tip 73 and one or more side openings 75 for directing the drug substantially laterally from the distal tip 64 into the tissue region. Preferably, the distal tip 64 also has a sufficiently small gauge diameter such that the passage 123 between the vessel 102 and the tissue region 100 is substantially self-sealing to prevent escape of the drug from the tissue region back into the vessel 102 upon removal of the distal tip 64.

Figure 5B:
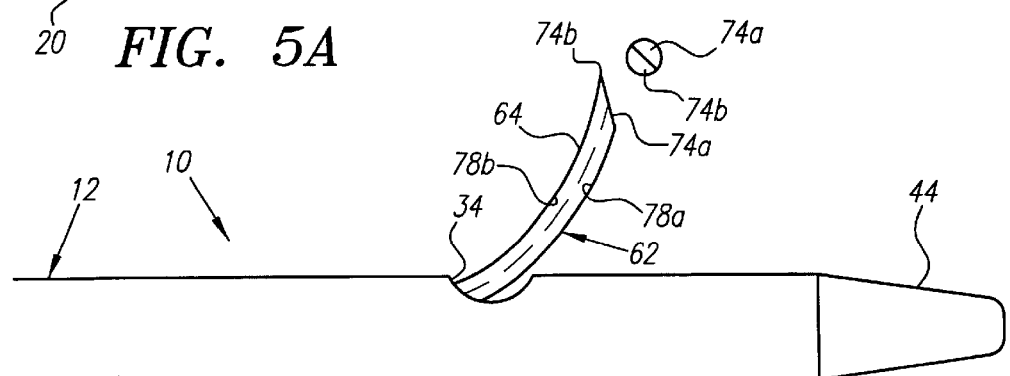
FIG. 5B is a side view of another alternative embodiment of the distal portion, including a dual lumen needle assembly.
Figure 5C:
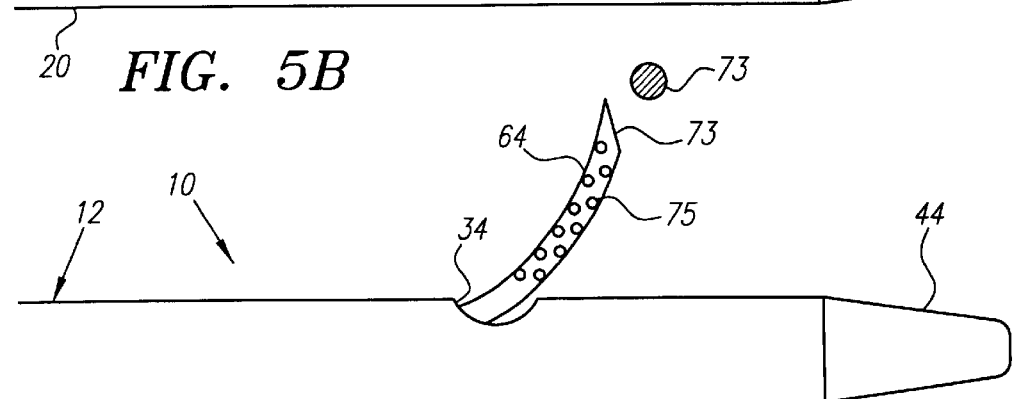
FIG. 5C is another alternative embodiment of the distal portion, including a plurality of outlet ports for providing a predetermined flow pattern.

Alternatively, as shown in FIG. 5B, the needle assembly 62 may include dual lumens 78*a*, 78*b* that extend between a multiple line manifold on the proximal end (not shown) to two adjacent outlet ports 74*a*, 74*b*. A dual lumen needle assembly may be useful for delivering a radiographic agent or other compound through one lumen in combination with a drug in the other. More preferably, the dual lumens may allow two drugs to be independently injected, which may then react with one another once within the selected tissue region, as will be appreciated by those skilled in the art.

The distal tip 64 may also be at least partially conductive, for example, by providing an electrode thereon (not shown) or by forming the distal tip 64 from a conductive material such as platinum, gold, or possibly stainless steel. A conductor, such as an electrically conductive wire (not shown), may extend proximally from the distal tip 64 through the tubular member 63 to the safety clip 66 of the needle assembly 62. A source of electric current may then be coupled to the conductor to enhance absorption of the drug by the tissue region. For example, the distal tip 64 may facilitate electroporation, i.e. energizing the distal tip 64 may create microscopic pores in the surrounding tissue to enhance penetration of the drug therein.

Figure 2:
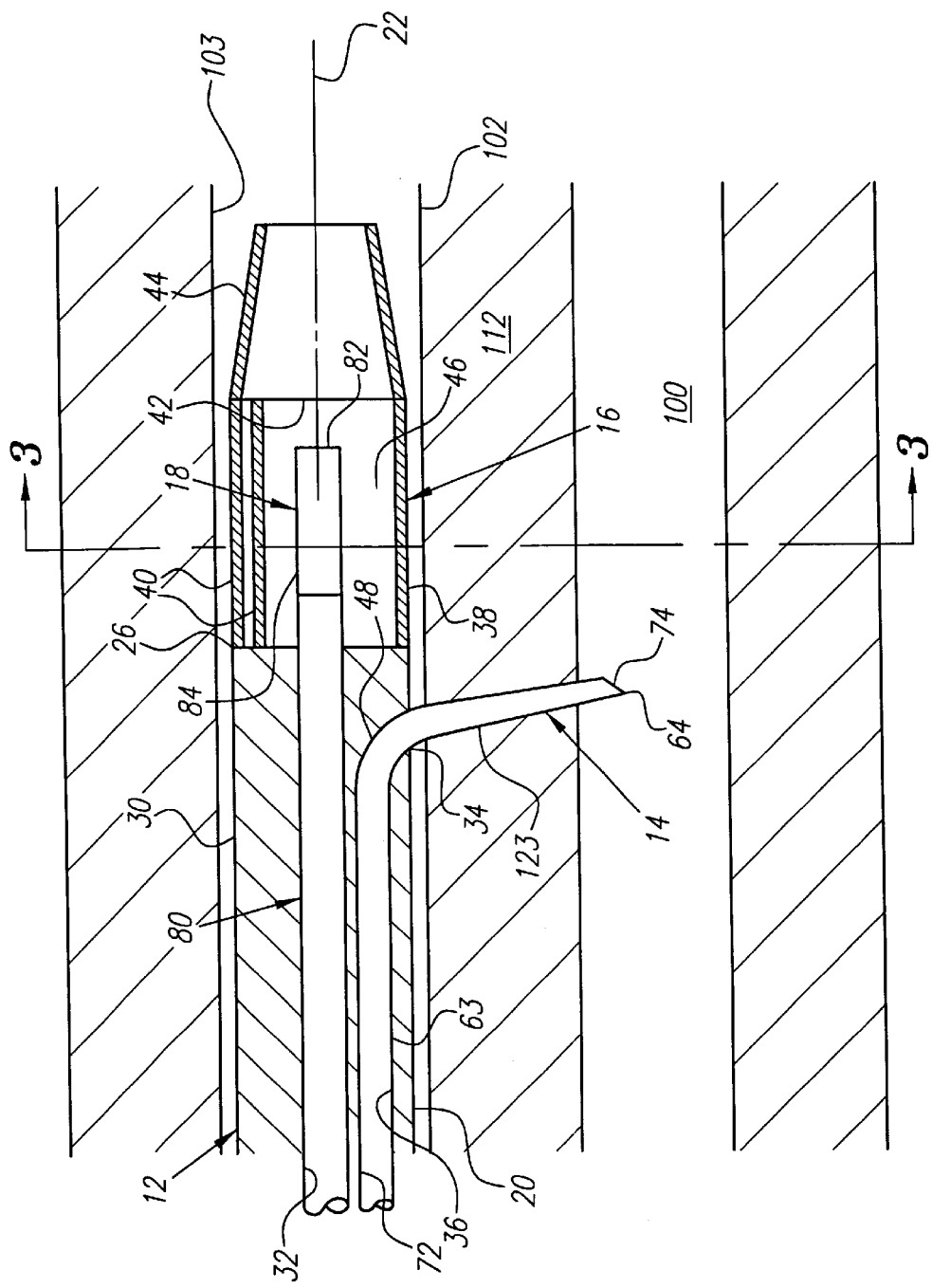
FIG. 2 is a cross-sectional view of the distal portion of the transvascular catheter system of FIG. 1, showing the needle assembly deployed into a remote blood vessel.

With respect to the imaging element 18, in a first preferred embodiment best seen in FIG. 2, an intravascular ultrasound ("IVUS") device 80 is provided. A conventional ultrasound transducer 82 is provided on the distal end 84 of the IVUS device 80 that is oriented towards an imaging plane substantially normal to the longitudinal axis 22. The ultrasound transducer 82 or a reflector on the IVUS device 80 (not shown) may be rotatable about the longitudinal axis 22 to provide ultrasonic image slices along the imaging plane in a conventional manner, or alternatively, a phased array of ultrasound transducers may be provided to allow imaging along a plane substantially normal to the longitudinal axis 22, as will be appreciated by those skilled in the art. Further information on the use of an IVUS device for imaging tissue and other surrounding landmarks from within a blood vessel may be found in "Transvenous Coronary Ultrasound Imaging—A Novel Approach to Visualization of the Coronary Arteries" by Sudhir et al., the disclosure of which is expressly incorporated herein by reference.

During use, the transvascular catheter system 10 may be used to deliver a drug to a selected remote tissue region within a patient's body in the following manner. The catheter 12 may be introduced percutaneously into a blood vessel in a conventional manner, while the needle assembly 62 remains retracted within the needle lumen 36, i.e. while the distal tip 64 is positioned within the needle lumen 36 proximal to the deflecting element 48. The distal portion 30 of the catheter 12 may be directed endovascularly to a vessel location adjacent to a remote tissue region for which treatment is selected.

Figure 3A:
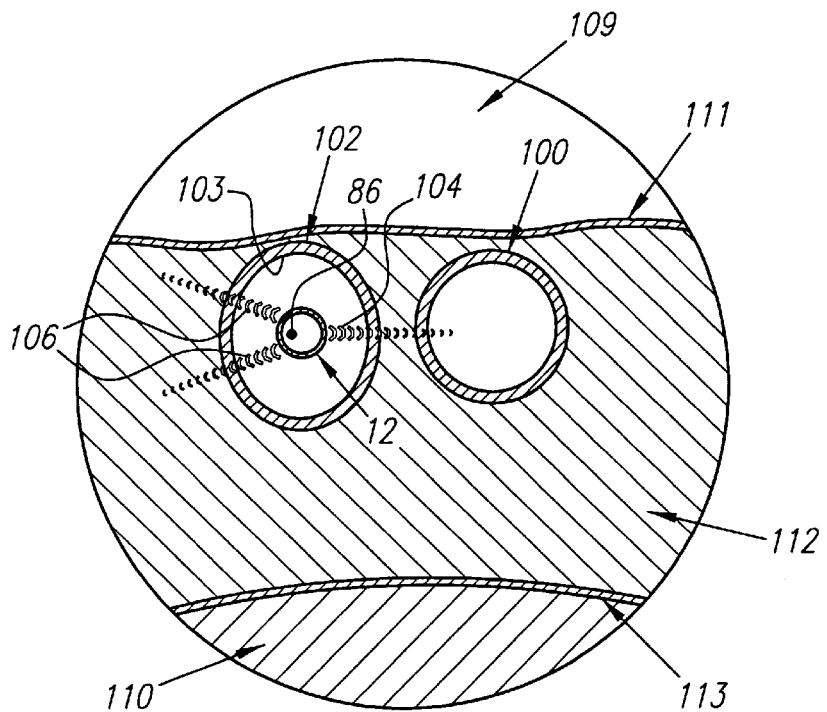
FIG. 3A is a cross-sectional view of the transvascular catheter system and surrounding heart tissue of FIG. 2, taken along line 3—3 using an internal imaging element, showing artifacts directing the catheter towards another blood vessel.

For example, in one preferred method shown in FIGS. 2 and 3A, the catheter 12 may be directed through the patient's venous system to a coronary vein 102 adjacent to a coronary artery 100 selected for treatment. In another preferred method shown in FIGS. 6 and 3B the catheter 12 may be directed to a location within a coronary vein 102 adjacent to a selected ischemic region 220 of the myocardium 112 for delivering a drug therein. Once the desired endovascular location is reached, the catheter 12 may be oriented towards the selected tissue region using ultrasound imaging with the IVUS device 80, external imaging, such as fluoroscopy, or both.

Turning to FIGS. 2 and 3A, the IVUS device 80 is shown being used to orient the system 10 for delivering a drug into a coronary artery 100 from a nearby coronary vein 102. The distal portion 30 of the catheter 12 is directed endovascularly through the venous system, for example over a guidewire 86, until it is within the coronary vein 102 and adjacent the selected coronary artery 100. The ultrasound transducer 82 may then be operated to provide a cross-sectional image of the region, shown illustratively in FIG. 3A. The resulting image aids the user in orienting the catheter 12 with respect to the tissue surrounding the vein 102, for example to identify landmarks such as the pericardium 109, the endocardium 111, the epicardium 113, and/or the heart chamber 110. Further, because the struts 38, 40 are opaque to the ultrasound transducer 82 (not shown in FIG. 3A), they produce artifacts 104, 106 on the image, thereby providing the orientation of the distal portion 30 of the catheter 12 with respect to the surrounding myocardium 112 and the selected coronary artery 100.

More particularly, because of the triangular arrangement of the struts 38, 40, their artifacts 104, 106 "point" circumferentially in the direction of the periphery 20 corresponding to the location of the peripheral opening 34, and consequently in the direction towards which the distal tip 64 of the needle assembly 62 will be deployed from the catheter 12. The catheter 12 may be torqued about its longitudinal axis 22 to rotate the distal portion 30, as observed by the artifacts 104, 106, until it can be seen that the distal tip 64 of the needle assembly 62, i.e. the artifact 104, is directed towards the selected the coronary artery 100.

The resulting ultrasound image may also be scalable, allowing the user to measure the distance to the selected target region from the catheter 12, and thereby determine the precise distance that the distal tip 64 of the needle assembly 62 will need to be directed to reach the selected tissue region. The needle stop 70 on the handle 50 may then be loosened, adjusted along the graduated region 60, and then locked at a predetermined position corresponding to the precise distance.

Once the catheter 12 is properly oriented and the needle stop 70 is locked at the predetermined position, the distal tip 64 of the needle assembly 62 may be deployed from the catheter 12 to penetrate the wall 103 of the vessel location 102 and enter the selected tissue region 100. Preferably, the needle thumb slide 68 is directed distally by the user, thereby directing the distal tip 64 against the deflecting element 48 and causing the distal tip 64 to deflect radially outward as it exits the peripheral opening 34.

Because of the secured position of the needle stop 70 on the handle 50, the needle thumb slide 68 may be quickly advanced distally until it abuts the needle stop 70, thereby puncturing the wall 103 of the vein 102 and delivering the distal tip 64 the precise distance, i.e. precisely within the selected target region of the artery 100. Alternatively, it may be desirable to overshoot, i.e. pass a predetermined distance through and beyond the selected target region, and then slowly withdraw the distal tip 64 until it reaches the selected tissue region.

A drug may then be introduced into the selected tissue region, for example by connecting a source of the drug such as a syringe (not shown), to the proximal end (not shown) of the needle assembly 62, and injecting the drug through the lumen 72 and the outlet 74 in the distal tip 64. The distal tip 64 may then be withdrawn back into the needle lumen 36 and the catheter 12 withdrawn from the patient in a conventional manner.

Prior to delivering the drug, a "mapping" procedure may be used to ensure that the drug will be delivered as desired into the specific tissue region selected for treatment. For example, a radiographic agent may be delivered through the outlet 74 in the distal tip 64. The flow of the radiographic agent may be observed with respect to the selected tissue region, for example using fluoroscopy. Once it has been confirmed that the radiographic agent flows as desired into the selected tissue region, the drug may then be introduced, thereby possibly avoiding misdelivery of what are often quite expensive drugs. Alternatively, a radiographic agent and the like may be mixed with the drug to track the flow of the drug within the body, particularly with respect to the selected tissue region.

Figure 6:
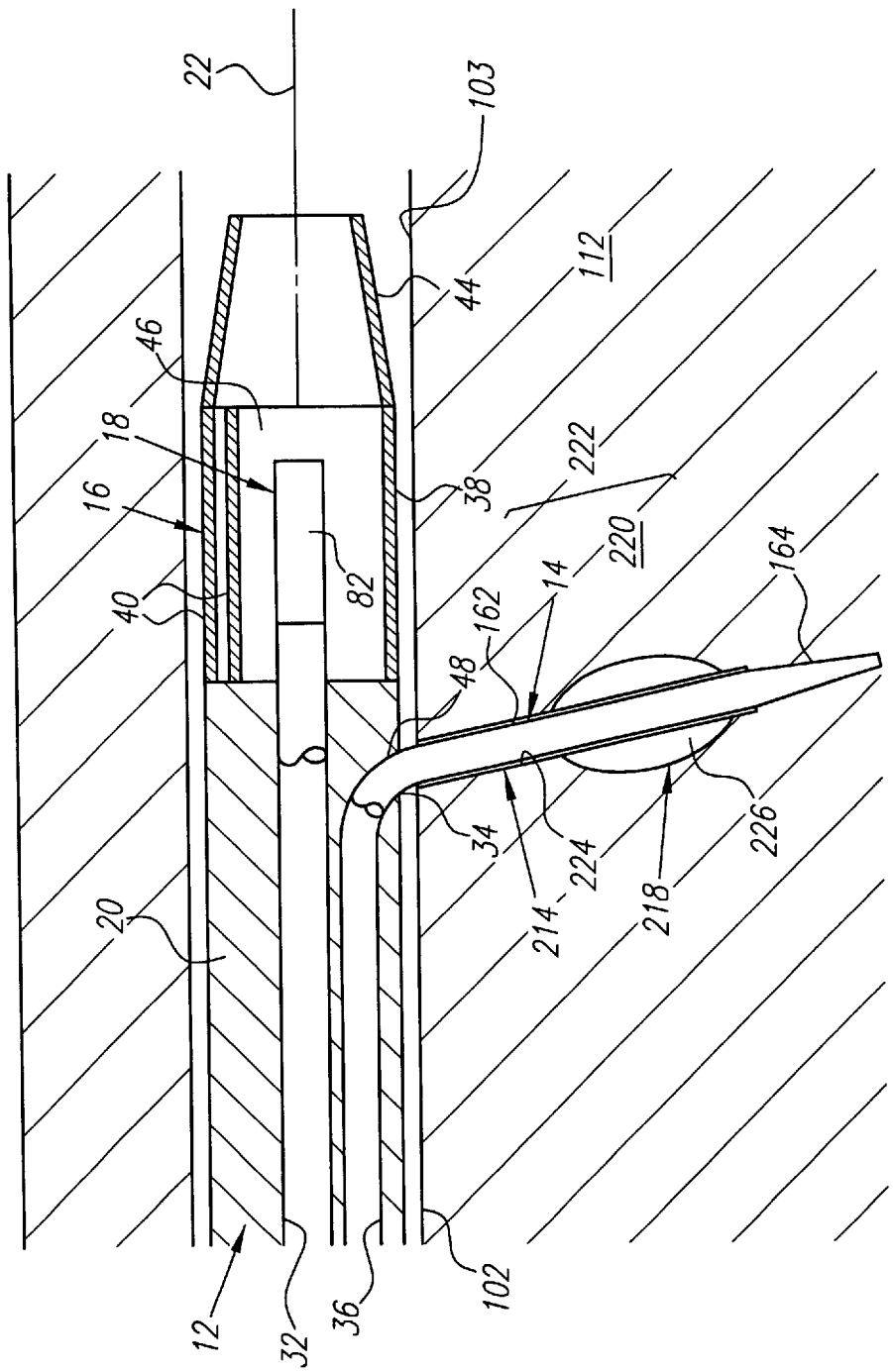
FIG. 6 is a cross-sectional view of another preferred embodiment of a transvascular catheter system in accordance with the present invention, including a guide wire assembly and a drug delivery catheter deployed into a remote tissue region.

Turning now to FIG. 6, another preferred embodiment of a transvascular catheter system 10 for delivering a drug to a remote tissue region 220 within the myocardium 112 is shown. Several of the elements are similar to those previously described and consequently have the same reference numbers and will not be described further. The system 10 of this embodiment includes a drug delivery element, namely a drug delivery catheter 2.14, that ay be deployed from the distal portion 30 of the catheter 12, preferably in combination with the puncturing element 14.

The puncturing element 14 preferably includes a solid needle or guide wire assembly 162, without a lumen but otherwise similar to the needle assembly 62 previously described, over which the drug delivery catheter 214 may be deployed. The guide wire assembly 162 may include an anchoring tip (not shown) for fixing the distal tip 164 of the guide wire assembly 162 in the tissue region 220 and/or to facilitate introduction of instruments, such as the drug delivery catheter 214, to the tissue region 220.

The drug delivery catheter 214 may include a porous balloon 218 for infusing the drug in a predetermined pattern within the tissue region 220, and generally includes a plurality of lumens extending between its proximal portion (not shown), and a distal portion 222. The drug delivery catheter 214 preferably has a guide wire lumen 224 such that the drug delivery catheter 214 may be delivered to the tissue region 220 over the guide wire assembly 162, and also has a drug delivery lumen (not shown) communicating with a portion, e.g. the interior, of the porous balloon 218. The porous balloon 218 includes a porous region, such as a plurality of holes 226, a permeable membrane and the like, preferably arranged to provide a predetermined flow pattern through the balloon 218 into the tissue region 220.

Figure 3B:
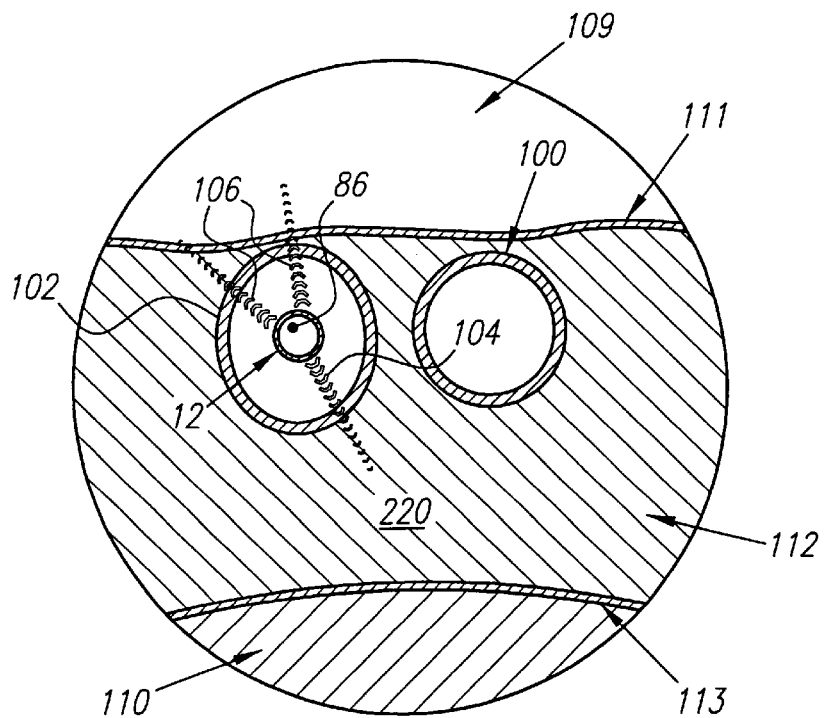
FIG. 3B is a cross-sectional view of the transvascular catheter system and surrounding heart tissue, similar to FIG. 3A, but showing artifacts directing the catheter towards the myocardium of the heart.

During use, the catheter 12 may be introduced percutaneously into a blood vessel 102, and oriented with respect to the selected tissue region 220 (see FIG. 3B). The guide wire assembly 162 may then be deployed transvascularly to access the selected tissue region 220, similar to the process previously described. The drug delivery catheter 214 may then be advanced over the guide wire assembly 162 until it enters the tissue region 220. The balloon 218 may then be inflated, expanding it from a collapsed condition around the drug delivery catheter 214 to an enlarged condition contacting the surrounding tissue 220. The balloon 218 may be inflated simply by introducing a drug through the drug delivery lumen, which may then seep through the porous region 226 and pass into the tissue region 220. Alternatively, the catheter 214 may include a separate inflation lumen (not shown) through which an inflation media such as saline may be introduced into a non-porous region within the balloon isolated from the porous region, as will be appreciated by those skilled in the art. In a further alternative, the drug delivery element may be a flexible, thin, floppy catheter which may be left behind to serve as an "indwelling" transcutaneous access catheter, as described more particularly below.

In further alternatives, the drug delivery catheter 214 and/or the guide wire assembly 162 may include an electrode or other element (not shown) to enhance penetration of the delivered drug into the tissue region. For example, an internal heating element (not shown) may be provided within the balloon 218 to heat the fluid therein and/or the surrounding tissue 220, which may enhance absorption of the drug delivered into the tissue. Alternatively, an electrode (not shown) may be provided on or within the balloon 218 which may be coupled to an external electrode (not shown). Direct current may then be applied between the electrodes to ionophoretically direct drugs from the drug delivery catheter 214 deep into the surrounding tissue 220. In a further alternative, the distal tip 164 of the guide wire assembly 162 may be formed from an electrically conductive material such as gold or platinum, or may include an electrode on a portion thereof (not shown), which may be coupled to an external source of electric current via a conductor (not shown) extending proximally through the guide wire assembly 162.

Thus, a transvascular catheter system 10 in accordance with the present invention may be used to deliver a single dose or bolus of a drug directly and precisely into a selected remote tissue region. Alternatively, the system may be used for sustained delivery by keeping the distal portion 30 of the catheter 12 and/or the distal tip 64 of the needle assembly 62 within the blood vessel and/or selected tissue region for an extended period of time.

For example, the needle assembly 62 or infusion catheter 214 may be used to inject a matrix material into a tissue region which may slowly diffuse a drug into the tissue region. Alternatively, a stent or similar structure may be delivered into the tissue region, the structure including a drug therein that may be released over time.

In addition, to provide sustained delivery and/or a series of treatments of a drug, an indwelling catheter (not shown) may be left behind within the selected tissue region. For example, the transvascular catheter system 10 may be introduced into a blood vessel, and the puncturing element 14, e.g. the needle assembly 62 or the guide wire assembly 162, may be oriented and deployed within a selected tissue region, such as an interstitial tissue region or another blood vessel.

A guide wire (not shown) may be advanced into the tissue region, and possibly anchored in place. The transvascular catheter 12 may be withdrawn from the blood vessel, leaving the guide wire, and a thin, floppy catheter (not shown), which may be an infusion catheter similar to that previously described or simply a single delivery port device, may be tracked over the guide wire into the tissue region and left there. The guide wire may then be removed, and the proximal end (not shown) of the thin, floppy catheter may be secured to the patient, for example taped or ported (such as using a port assembly such as that described below) depending upon the length of time therapy is desired. The distal end of the indwelling catheter may then remain in place within the tissue region, possibly for extended periods of time, to provide access whenever needed.

Figure 7:
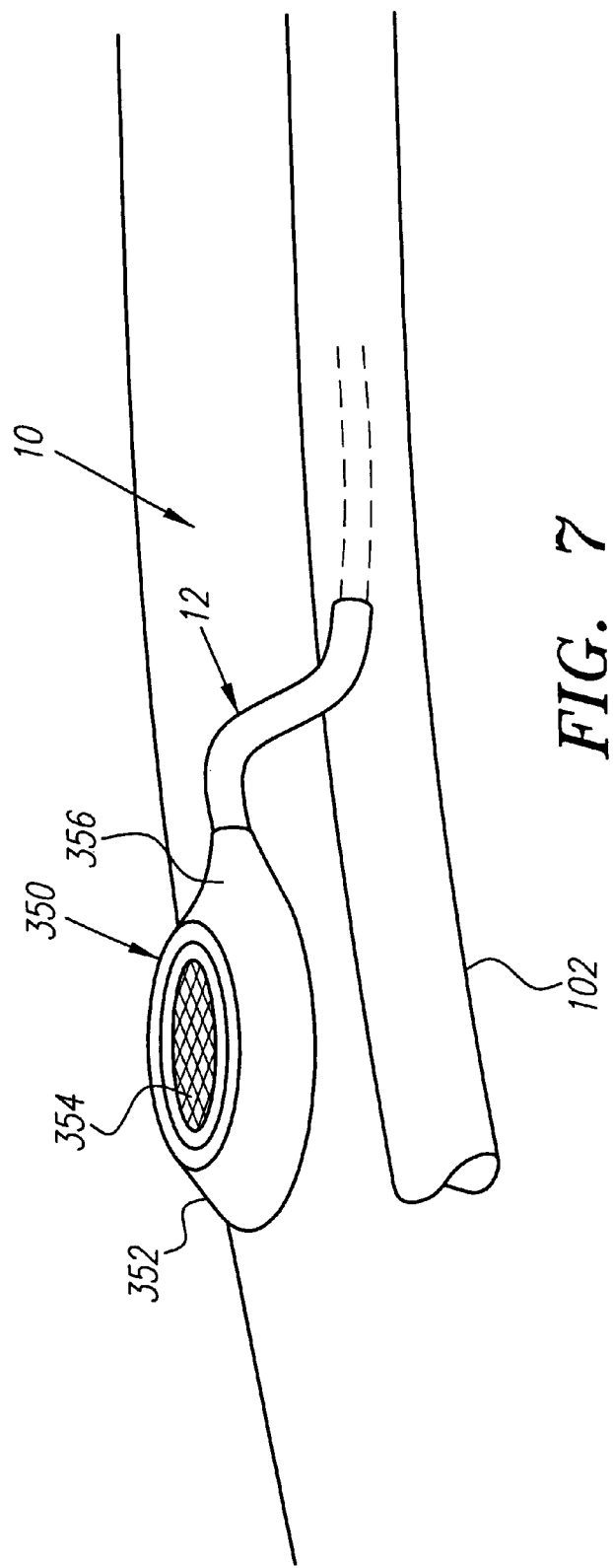
FIG. 7 is a perspective view of an implantable port assembly for use with a transvascular catheter system in accordance with the present invention.

Alternatively, turning to FIG. 7, the transvascular catheter system 10 may include an implantable port assembly 350.

The port assembly 350 includes a body 352 which may be implantable on or beneath the skin of the patient, and one or more seals 354. The body includes a hollow hub 356 the interior of which communicates with the seal 354 which may be attached to the transvascular catheter system 10, such as the proximal end 24 of the catheter 12 or preferably to an indwelling catheter (not shown).

For example, the catheter 12 shown in FIG. 1 may be percutaneously introduced into a patient's cardiovascular system, and the distal portion 30 may be advanced into a selected vessel, whereupon the distal tip 64 of the needle assembly 62 (not shown in FIG. 7) may be advanced into a selected remote tissue region, similar to the methods previously described. The handle 50 (not shown in FIG. 7) may then be removed from the proximal end 24 and replaced with the port assembly 350 such that the hub 356 may communicate with the needle lumen 36, the IVUS lumen 32, and/or a drug delivery lumen in the indwelling catheter. The port assembly 350 may then be stitched or otherwise implanted onto an accessible region of the patient's body (not shown).

Whenever it is desired to access the tissue region, an instrument such as a needle, an infusion device, a sensor and the like (not shown) may be directed through the seal 354 to communicate with the drug delivery element extending to the selected tissue region. For example, during gene or growth factor therapy, it is often desired to subject the selected tissue region to compounds, such as angiogenic growth factors, for extensive periods of time. The implantable system of the present invention facilitates such sustained treatment by allowing the tissue region to be accessed as often as necessary to maintain a desired level of growth factor at the selected tissue region.

Figure 8:
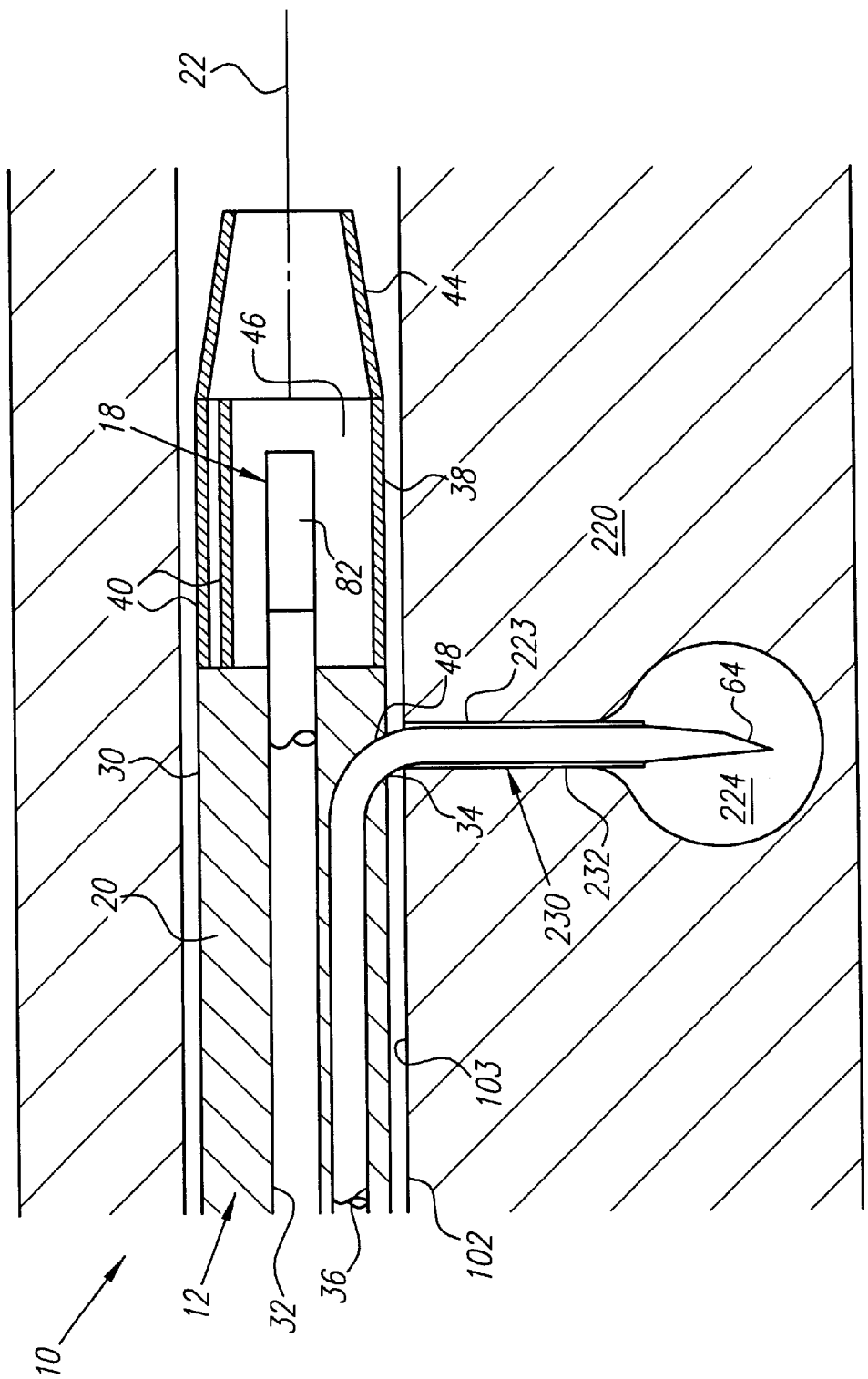
FIG. 8 is a cross-sectional view of another preferred embodiment of a transvascular catheter system, including a guide wire assembly and an ablation device.

Turning now to FIG. 8, another preferred embodiment of a transvascular catheter system 10 in accordance with the present invention is shown, which may be used to create a drug reservoir 224 within a selected tissue region 220 itself to provide sustained delivery. A catheter 12, similar to that previously described, may be introduced endovascularly into a blood vessel 102 until the distal portion 30 is adjacent the tissue region 220. The distal tip 64 of the needle assembly 62 may be oriented and deployed to puncture the wall 103 of the vessel 102 and enter the tissue region 220, using methods similar to those described above.

An ablation device 230, such as a radio frequency (RF) device, a laser device, and the like, may be advanced over the needle assembly 62 into the tissue region 220. One or more electrodes 232 or similar elements on the ablation device 230 may be activated to create a cavity 224 within the tissue region 220 in a manner known to those skilled in the art. The ablation device 230 may then be removed, and a drug may be introduced into the cavity 224 to create a drug reservoir in continuous contact with the surrounding tissue 220, thereby providing sustained delivery as the drug is slowly absorbed by the surrounding tissue 220.

As an alternative to ablation of tissue, a non-porous balloon catheter (not shown) may be advanced over the needle assembly 62 into the tissue region 220. The balloon may be inflated to its enlarged condition to contact and push aside the surrounding tissue 220, and create a cavity 224. No additional treatment of the tissue 220 may be needed to create the cavity 224, particularly in ischemic tissue which is substantially non-resilient as compared to healthy tissue and unlikely to expand back to fill the cavity 224. It is also within the spirit of the present invention that other devices, such as cutting, coring or other mechanical instruments, may also be used to remove tissue to create the cavity 224 by being advanced over the needle assembly 62 into the tissue region 220, as will be appreciated by those skilled in the art.

In addition, it may be desirable to inject a sealant or matrix material, such as collagen or a filament structure (e.g. drug-impregnated suture material), into the cavity 224 or into the passage 223 extending between the blood vessel 102 and the cavity 224. Although the distal tip 64 may be sufficiently small so as to create a self-sealing passage 223, advancement of instruments, such as the drug delivery catheter 214 of FIG. 6, may dilate the passage 223, which may result in the drug leaking through the passage 23 back into the blood vessel 102 from the cavity 224. To substantially reduce the risk of this occurring, a sealant, matrix material, or filament (not shown) may be injected into the cavity 224 itself, or into the passage 223, for example through a lumen in the drug delivery element 214 or the needle assembly 62 before or while it is being withdrawn from the cavity 224.

In a further alternative shown in FIG. 5A, the transvascular catheter system 10 may include a plurality of needle assemblies 62, similar to the individual needle assembly described above, to be deployed in a predetermined arrangement along the periphery 20 of the catheter 12. Preferably, the needle assemblies 62 are arranged axially in a row, aligned with the strut of the "cage" structure orientation element (not shown in FIG. 5A). In particular, it may be desirable to access an extended remote tissue region, for example extending substantially parallel to a vessel, especially within the myocardium. With a multiple needle transvascular catheter system, a single device may be delivered into a vessel and oriented. The array of needles may be sequentially or simultaneously deployed to inject one or more drugs into the extended tissue region, thereby providing a selected trajectory pattern.

Other directional drug delivery elements may also be provided within the present invention. For example, a catheter having a drug delivery element, an orientation element and possibly an imaging element may be provided similar to those described above. Instead of a needle or guide wire assembly, the distal portion of the catheter may include an osmotic surface on a portion of the circumference or periphery and extending axially along the distal portion (not shown).

The osmotic surface preferably has a predetermined relationship to the orientation element, such that the osmotic surface may be directed circumferentially towards a selected tissue region, e.g. a specific portion of a vessel wall and/or a tissue region beyond the vessel wall. The catheter may include a balloon or other expandable structure which may push the osmotic surface into direct contact with the vessel wall to further facilitate delivery. A drug, possibly embedded within the osmotic surface itself or in a chamber beneath the osmotic surface, may then be delivered with or without ionophoresis or other assisted delivery mechanism.

Figure 13:
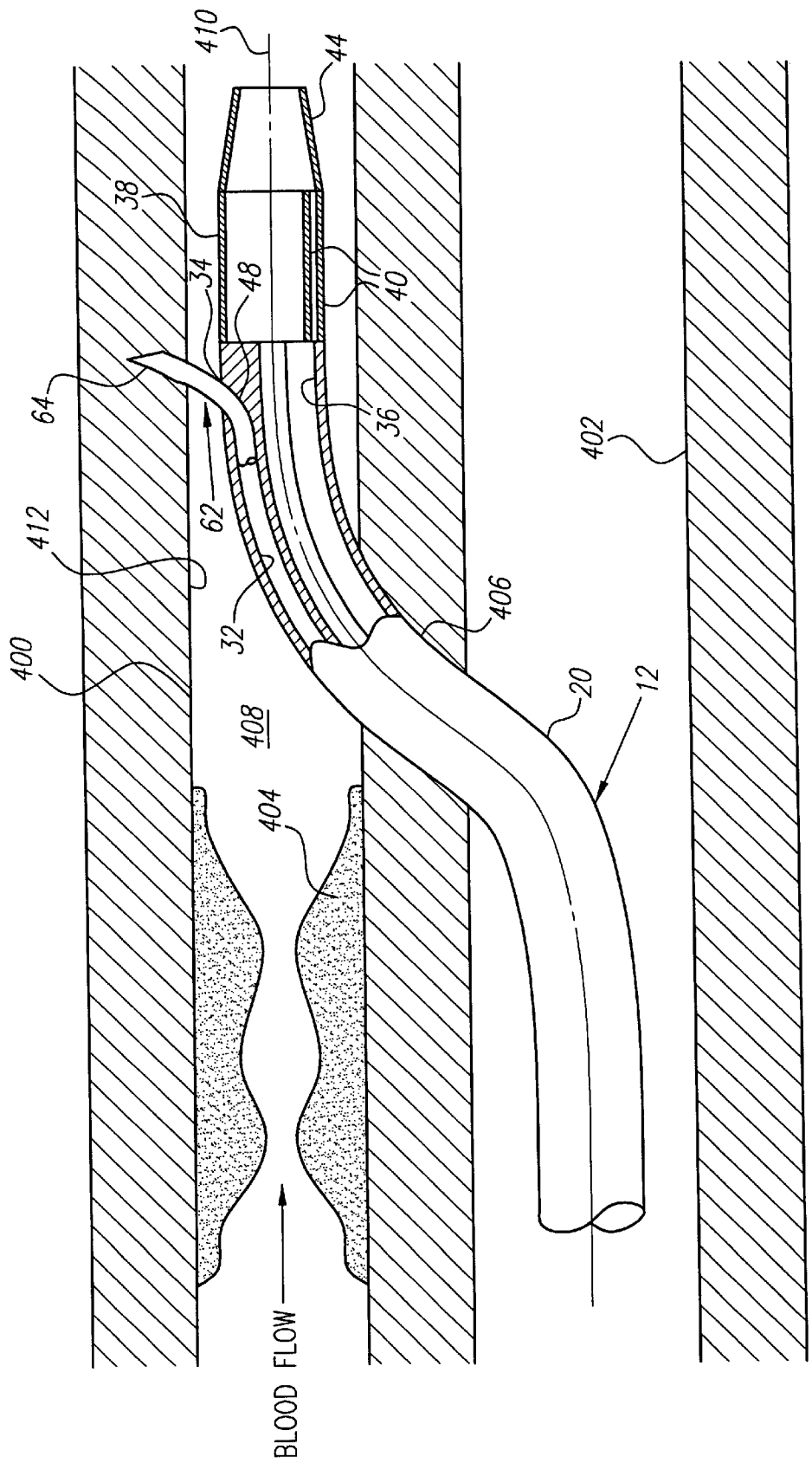
FIG. 13 is a cross-sectional view of a transvascular catheter system in accordance with the present invention delivered downstream of a stenotic region in a blood vessel.

Turning to FIG. 13, the systems and methods of the present invention may also be used to provide access downstream of an occluded or stenotic region of a blood vessel, for example to treat a coronary artery or ischemic tissue region of the myocardium downstream of an occluded coronary artery. First, a location downstream of an occluded section 404 of a coronary artery 400 may be selected for treatment, and a transvascular catheter device (not shown) percutaneously introduced into the venous system and advanced until it reaches a coronary vein 402 adjacent the selected artery 400. An interstitial passage 406 may be created between the coronary vein 402 and the coronary artery 400, and a guide wire 410 may be advanced through the interstitial passage 406 into the coronary artery 400. The guide wire 410 may be substantially anchored within the coronary artery 400, for example by embedding the distal end of the guide wire 410 into the wall of the coronary artery 400 (not shown). Further details on the systems and methods for performing interstitial or transvascular procedures between the venous and arterial systems may be found in co-pending application Ser. Nos. 08/730,327 and 08/730,496, both filed Oct. 11, 1996, the disclosures of which are expressly incorporated herein by reference.

A transvascular catheter system 10, similar to those previously described, may then be advanced over the guide wire 410 along the venous system, through the interstitial passage 406 and into the coronary artery 400 downstream of the occluded region 404, thus without disturbing plaque or otherwise affecting flow through the arterial system. It will be appreciated by those skilled in the art that the transvascular catheter system 10 used to deliver the drug may also be used to create the interstitial passage 406.

The artery 400 itself may then be treated, for example, using the needle 62 of FIG. 1 or the drug delivery catheter 214 of FIG. 6. A drug may be delivered into the lumen 408 of the artery 400, into the vessel wall 412 and/or the surrounding tissue 414. In addition, one or more drug reservoirs (not shown) may be created within the surrounding tissue 414, most preferably within myocardial tissue adjacent to a coronary artery, for receiving a drug that may be absorbed by the surrounding tissue 414 over an extended period of time.

Other useful features may also be included in any of the embodiments of the transvascular catheter system 10 in accordance with the present invention. For example, the catheter 12 may include one or more stabilizing balloons (not shown) on the distal portion 30, for example proximal to the peripheral opening 34. An inflation lumen may be provided in the catheter 12 to allow an inflation medium, e.g. saline, to be introduced into the stabilizing balloon to substantially anchor the catheter 12 at a desired location within the blood vessel, i.e. to prevent the catheter 12 from moving axially within the vessel once the distal portion 30 is adjacent to a remote tissue region selected for treatment.

In addition, one or more of the elements of the system may include a sensor for measuring information relevant to the treatment of the selected tissue region. For example, a pressure sensor may be provided on the catheter 12, the needle assembly 62 and/or the drug delivery element. A lumen may extend proximally through the respective element, thereby allowing the user to continuously monitor pressure at or near the delivery site. The drug delivery element may also include a flow measurement sensor, allowing the amount of drug being delivered to the selected tissue region to be precisely measured.

Figure 5D:
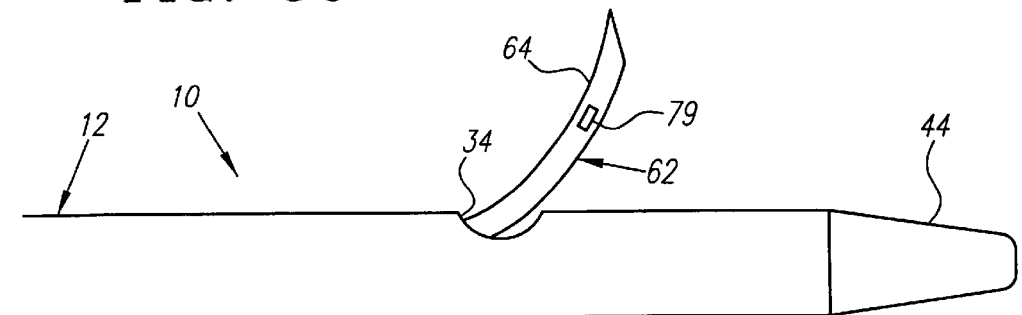
FIG. 5D is another alternative embodiment of the distal portion, including a feedback sensor on the needle assembly.

Other feedback elements may also be provided, for example, a thermocouple or other temperature sensor may be provided on systems including ionophoresis electrodes or ablation devices to monitor the amount of heating being experienced by tissue during a procedure. Alternatively as shown in FIG. 5D, the needle assembly 62 or other component may include a feedback element 79 for measuring a physiological condition. For example, an EKG lead may be included on the distal tip or otherwise delivered within the selected tissue region, thereby allowing electrical events within the heart to be monitored during drug delivery. During treatment, for example, a drug may be delivered into a tissue region until a desired condition is met, such as until the tissue becomes non-tachycardic, or until tachycardia is induced.

An important aspect of the transvascular catheter system of the present invention is the ability to precisely deliver a drug to a selected remote location within a reference frame, preferably including a circumferential or peripheral component and a radial component. The orientation element provides the peripheral component because of its predetermined relationship with the periphery of the catheter and the drug delivery element. The imaging element preferably provides the radial component by detecting the relationship of the orientation element to the selected remote location (e.g. the distance between them), or landmarks in a known relationship with the selected remote location. Once the location of the selected remote location is known within the reference frame, the drug delivery element may be directed towards the selected remote location for precise delivery of a drug.

In another aspect of the present invention, FIGS. 9A–9D and 10 show a preferred embodiment of an implantable reservoir device 400 that may be used to provide sustained delivery of a drug to tissue surrounding a blood vessel, preferably within a coronary vein 102 adjacent to ischemic myocardial tissue 112. The reservoir device 400 includes a substantially cylindrical frame 402 adapted to expand between a collapsed condition for insertion into a blood vessel and an enlarged condition for engaging a wall 103 of the blood vessel 102, and defining a longitudinal axis 404.

The frame 402 is sufficiently flexible to expand between the collapsed and enlarged conditions during use without substantial risk of failing or fatiguing, yet sufficiently rigid to anchor the reservoir device 400 within the blood vessel 102. Preferably, the frame 402 is resiliently biased towards the enlarged condition to prevent substantial movement of the frame 402 axially within the blood vessel 102. The frame 402 may be formed from a woven mesh of wire of, for example, a shape memory alloy such as Nitinol, stainless steel, platinum, polymers or other plastics and the like. The frame 402 may be woven into a criss-cross structure, a sinusoidal structure, or may include a pair of expandable rings connected by spacers to retain the rings apart axially.

A flexible membrane 408 is attached to the frame 402, preferably to the exterior of frame 402 such that the membrane 408 may enhance a fluid-tight seal when pressed against the wall 103 of the vessel 102 by the frame 402 after deployment. The membrane 408 includes a periphery 412 and end panels 414, 416, which together define a sealed reservoir 410 within the membrane 408 and the frame 402. The membrane 408 should be substantially flexible, and may be elastic if tension over the frame is preferred, or plastic if a small initial diameter is preferred. Preferred materials include dacron and PTFE, which may also be silicone dipped.

The membrane 408 includes a porous region 418, which is preferably disposed along at least a portion of the periphery 412 of the membrane 408. The porous region 418 may be a permeable or semi-permeable material bonded or otherwise attached to non-permeable segment(s) of the membrane 408. Alternatively, the entire membrane 408 may be formed from a non-permeable material with holes formed through discrete areas to define the porous region 418.

Figure 9A:
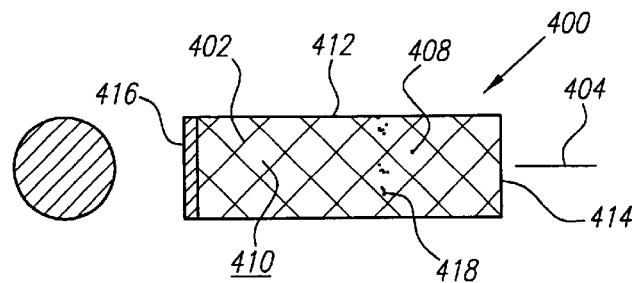
FIG. 9A is a side view of an implantable endovascular drug reservoir device in accordance with the present invention.
Figure 9B:
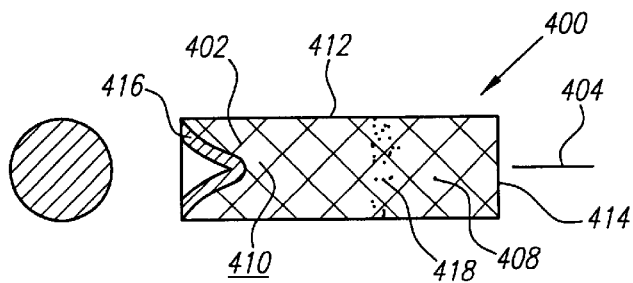
FIG. 9B is a side view of another embodiment of an implantable endovascular drug reservoir device, including a recrossable end panel.
Figure 9C:
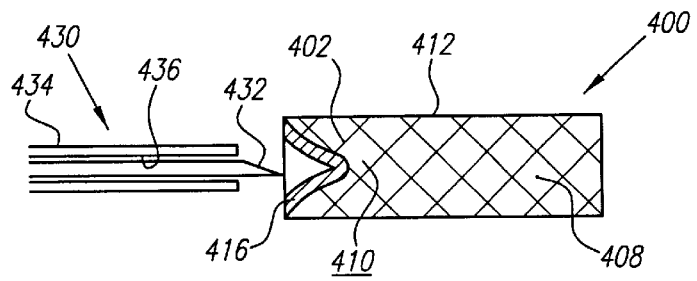
FIGS. 9C and 9D are side views of the implantable endovascular drug reservoir device of FIG. 9B, showing an injection device for filling the reservoir.

In addition, as shown in FIGS. 9B and 9C, at least one of the end panels 416 may be recrossable, i.e., may be penetrable by a needle 432, but automatically resealable, to facilitate in situ filling or refilling of the reservoir 410, preferably having a concave shape to facilitate penetration by the needle 432. Alternatively, the reservoir 410 may be prefilled with a drug, possibly together with an anticoagulant or other compound, prior to delivery into the blood vessel 422. In addition, the drug and the pore size of the porous region 418 may have a predetermined relationship such that the drug permeates or flows through the porous region 418 into the surrounding tissue at a predetermined flow rate.

During use, the reservoir device 400 is percutaneously delivered into a blood vessel in its collapsed condition using a delivery device, for example within a lumen of a delivery catheter or sheath adapted to receive the reservoir device 400. Alternatively, the frame 402 may include a control hub on one end (not shown), which may be gripped and compressed radially inward to collapse the frame 402.

Once the reservoir device 400 is in a blood vessel adjacent the target region, such as the coronary vein 102 adjacent to the selected tissue region 112, the reservoir device 400 is deployed from the delivery device, for example using a plunger within the delivery catheter lumen (not shown). Preferably, the frame 402 automatically expands to its enlarged condition, thereby substantially anchoring the device 400 in position within the vessel 102. The frame 402 may also create a substantially fluid-tight seal with the wall 103 of the vessel 102, to prevent substantial leakage of fluid delivered through the periphery 412 downstream within the vessel 102.

Figure 9D:
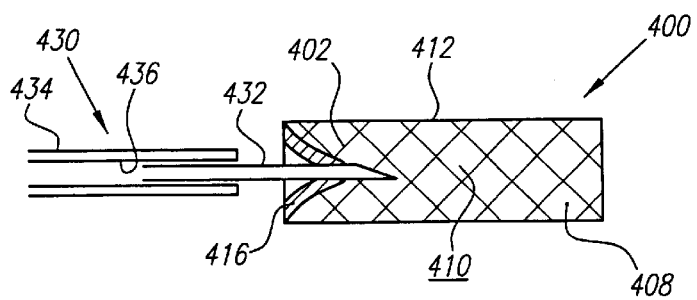

If the reservoir 410 is empty during deployment, for example, to prevent rupture of the membrane 408 when the frame 402 is collapsed, a drug delivery element may be introduced into the vessel 102 to fill the reservoir 410. For example, as shown in FIGS. 9C and 9D, an injection device 430 including a sheath 434 covering a hollow needle 432 may be delivered endovascularly, or the delivery catheter used to deliver the reservoir device 400 may include an additional drug delivery needle lumen. The needle 432 may be deployed to penetrate the recrossable end region 416, whereupon the reservoir 410 may be filled by introducing the drug through the needle 432.

The reservoir device 400 may remain in the vessel 102 for a substantial period of time, possibly hours or days, allowing the drug to slowly absorb into the wall of the vessel and preferably the surrounding tissue. In addition, the drug delivery element, e.g. the sheath-covered hollow needle, may be reintroduced into the vessel 423 to refill the reservoir 410, for example using an implantable port assembly similar to that shown in FIG. 7. Alternatively, the reservoir device 400 may include an electrode (not shown) to enable ionophoresis or other enhanced delivery. A catheter including a conductor (not shown) may be introduced into the vessel 102, coupled to the electrode, and then energized by an external source of electric current (not shown) for this purpose.

Figure 11:
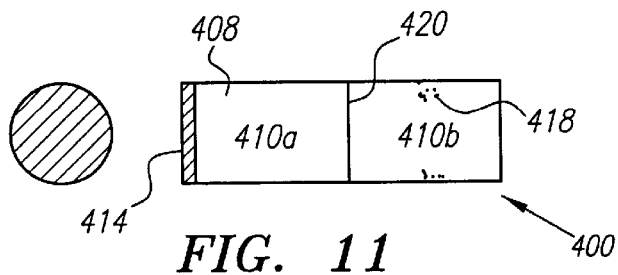
FIG. 11 is a side view of an alternative embodiment of an implantable endovascular drug reservoir device in accordance with the present invention.
Figure 10:
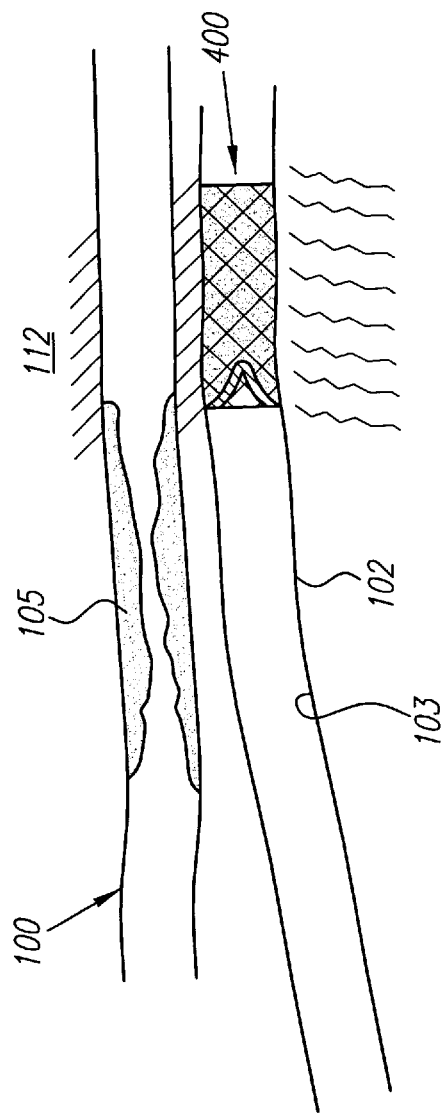
FIG. 10 is a cross-sectional side view of the drug reservoir device of FIG. 9A, deployed within a vein adjacent to a stenotic region of an artery.

In an alternative embodiment, shown in FIG. 11, the reservoir device 400 may provide an endovascular "pump" for time-release delivery of a drug. In this embodiment, the reservoir device 400 includes a septum panel 420 dividing the reservoir 410 into first and second regions 410a, 410b. The first end panel 414 of the membrane 408 is an osmotic membrane and the first reservoir 410a is filled with a fluid absorbing compound. The porous region 418 of the membrane 408 communicates only with the second reservoir 410b, which is filled with a drug in situ or before deployment.

When the reservoir device 400 is deployed within a vessel (not shown), using a procedure similar to that just described, the compound in the first reservoir 410a begins to slowly draw fluid osmotically from within the lumen of the vessel. As this occurs, the septum panel 420 is forced to expand towards the second end panel 416, thereby applying a force within the second reservoir 410b, which "pumps" or otherwise encourages the drug to flow out the porous region 418, and preferably into the wall of the vessel.

In other arrangements, instead of the septum panel 420, a cylindrical septum may be provided, creating an internal first reservoir and an annular second reservoir surrounding the first reservoir (not shown). The area of one or both end panels in contact with the internal first reservoir may be provided from an osmotic material, thereby creating a similar flow out of a porous region on the periphery of the membrane in communication with the annular second reservoir.

Other shapes and configurations of the reservoir device 400 may also be provided that may be deployed and substantially anchored adjacent a selected tissue region. In addition, a drug reservoir device similar to those described may be delivered directly into tissue, for example, using one of the transvascular catheter systems previously described, as will be appreciated by those skilled in the art.

Figure 12:
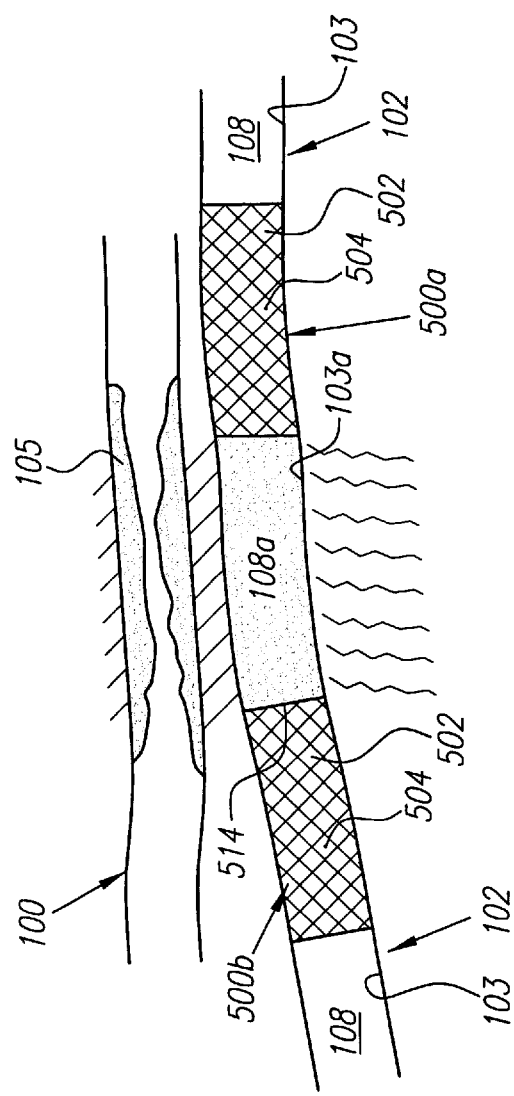
FIG. 12 is a side view of another implantable system in accordance with the present invention for creating a drug delivery reservoir, shown within a vein adjacent to a stenotic region of an artery.

In another preferred embodiment shown in FIG. 12, an implantable system including a pair of endovascular blocker devices 500 may be used to create a drug reservoir 508a within a blood vessel 102 itself, i.e. between the blockers 500 and the wall 103a of the vessel 102 between them. The blockers 500 preferably include an expandable frame 502 and a flexible membrane 504 attached to the frame 502, similar to that described above. The membrane 504, however, is preferably non-permeable, although alternatively a permeable periphery (not shown) may be provided to increase the surface area through which the drug may be directed towards the vessel wall 103.

To create the reservoir 508a, the first blocker 500a is deployed within a vessel 102 adjacent a selected tissue region, such as a stenotic region 105 within an artery 102, using a method similar to that described above for the reservoir device 400. A drug is introduced into the vessel lumen 108a, and a second blocker 500b is deployed within the vessel 102, thereby encapsulating the drug in the lumen 108a between the blockers 500a, 500b.

Alternatively, the drug may be delivered into the reservoir 508a after both blockers 500 are deployed and in secured within the vessel 102. For example, the second blocker 500b may include a recrossable end panel 514 on one end, and an open interior that may communicate directly with the reservoir 108a. Thus, an injection needle device (not shown) may be used to inject the rug through the recrossable end panel 514 and into the reservoir 508a in situ.

It has been determined clinically that one or more segments of the venous system, even within the coronary system, may be occluded for extensive periods of time without adversely affecting the performance of the coronary system. Accordingly, an implantable reservoir system in accordance with the present invention may be used to create a reservoir within a coronary vein without interfering substantially with the flow of return blood from the myocardium. A drug within the reservoir may then be absorbed by the vessel wall and surrounding tissue to treat selected tissue regions adjacent the reservoir site.

Of further note, it has been clinically determined that complete occlusion and shutdown of the coronary venous system may not impair normal operation of the heart. The endocardial veins may take over at least a portion of the additional venous return. Furthermore, within thirty minutes of complete occlusion, the Thebesian system, which includes capillaries, venals and porous tissue that makes up the myocardium itself, may replace the venous system and return one hundred percent of the return blood from the myocardium. Thus, the reservoir devices in accordance with the present invention may be deployed in one or more regions within the coronary venous system without substantial risk of adversely affecting coronary blood flow or damaging the tissues of the coronary system.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A system for delivering a substance towards a target region within a patient's body, the system comprising:
    a catheter having a proximal portion and a distal portion adapted for insertion into a blood vessel, and defining a periphery and a longitudinal axis;
    a rotational orientation element on the distal portion in a predetermined circumferential relationship with the periphery of the catheter for providing a peripheral orientation of the distal portion about the longitudinal axis;
    a drug delivery element on the distal portion for delivering a substance towards the target region beyond a wall of the blood vessel, the drug delivery element being aligned with the peripheral orientation of the orientation element; and
    an imaging element adjacent the orientation element for detecting the rotational orientation of the orientation element with respect to the target region.

2. The system of claim 1, wherein the drug delivery element comprises a needle deployable from the distal portion.

3. The system of claim 2, wherein the needle is deployable substantially radially from the distal portion.

4. The system of claim 3, further comprising a control mechanism on the proximal portion of the catheter linked to the needle for deploying the needle a precise distance radially from the distal portion, whereby the needle may be precisely deployed to a selected region remote from the catheter within a reference frame including a peripheral component and a radial component.

5. The system of claim 1, wherein the orientation element has an asymmetric configuration aligned with the drug delivery element for providing the peripheral orientation about the longitudinal axis.

6. The system of claim 1, wherein the orientation element comprises a cage structure including a plurality of struts extending axially along the distal portion.

7. The system of claim 1, wherein the orientation element comprises a first strut at a location in direct axial alignment with the drug deliver element.

8. The system of claim 7, wherein the orientation element further comprises a pair of struts opposite the first strut.

9. A system for delivering a substance to a target region within a patient's body, the system comprising:
    a catheter having a proximal portion and a distal portion adapted for insertion into a blood vessel, and defining a periphery and a longitudinal axis;
    a puncturing element deployable from the distal portion in a predetermined circumferential relationship with the periphery of the catheter, and including a distal tip adapted to penetrate a wall of a blood vessel to access a target region beyond the wall of the blood vessel;
    a drug delivery element on the distal portion for delivering a substance to the target region;
    a rotational orientation element on the distal portion in a predetermined relationship with the periphery of the catheter and the puncturing element; and
    an imaging element adjacent the orientation element for detecting the location of the orientation element with respect to the target region.

10. The system of claim 9, wherein the imaging element comprises an ultrasound transducer.

11. The system of claim 9, wherein the catheter includes a lumen extending from the proximal portion to the distal portion for receiving the imaging element therein.

12. The system of claim 9, further comprising:
    a handle on the proximal portion; and
    a control mechanism on the handle linked to the puncturing element for precisely advancing the puncturing element from the distal portion.

13. The system of claim 9, further comprising a peripheral opening at a predetermined circumferential location on the periphery of the distal portion through which the puncturing element may be deployed.

14. The system of claim 13, wherein the catheter includes a needle lumen communicating with the peripheral opening for receiving the puncturing element therethrough.

15. The system of claim 14, wherein the needle lumen includes a deflecting element adapted to direct the distal tip substantially transversely with respect to the longitudinal axis when the puncturing element is deployed.

16. The system of claim 9, wherein the drug delivery element comprises an indwelling catheter deployable in combination with the puncturing element to the tissue region.

17. The system of claim 9, wherein the puncturing element comprises a guide wire, and wherein the drug delivery element is deployable over the guide wire.

18. The system of claim 17, wherein the drug delivery element comprises an infusion catheter.

19. The system of claim 17, wherein the drug delivery element comprises a perfusion balloon.

20. The system of claim 17, wherein the guide wire includes an anchoring tip for fixing the guide wire in the tissue region.

21. The system of claim 17, wherein the drug delivery element includes an anchoring tip for fixing the drug delivery element in the tissue region.

22. The system of claim 9, wherein the drug delivery element includes a first electrode thereon adapted to be electrically coupled to a second electrode, whereby when direct current is directed between the first and second electrodes, a drug from the drug delivery element is ionophoretically directed from the drug delivery element towards the second electrode.

23. The system of claim 22, wherein the second electrode is attachable to a surface region of the patient being treated.

24. A system for delivering a drug towards a tissue region within a patient's body, the system comprising:
    a catheter having a proximal portion and a distal portion adapted for insertion into a blood vessel, and defining a periphery and a longitudinal axis;
    a rotational orientation element on the distal portion in a predetermined circumferential relationship with the periphery of the catheter for providing a peripheral orientation of the distal portion about the longitudinal axis;

a drug delivery assembly deployable from the distal portion and aligned with the peripheral orientation of the orientation element, the drug delivery assembly including a puncturing element for penetrating a wall of a blood vessel to access a tissue region beyond the wall of the blood vessel, and including a drug element comprising a lumen for delivering a drug to the tissue region; and an imaging element adjacent the orientation element for detecting the relationship of the orientation element with respect to the tissue region.

25. The system of claim 24, wherein the drug delivery assembly further comprises means for creating a cavity within the target region.

26. The system of claim 25, wherein the means for creating a cavity comprises a balloon.

27. The system of claim 26, wherein the drug delivery element comprises a drug delivery catheter having the balloon on a distal portion thereof.

28. The system of claim 27, wherein the balloon comprises a porous region in communication with the lumen.

29. The system of claim 24, wherein the puncturing element comprises a needle or a guide wire deployable from the distal portion of the catheter.

30. The system of claim 29, wherein the needle or guidewire is deployable substantially radially from the distal portion of the catheter.

31. The system of claim 30, further comprising a control mechanism on the proximal portion of the catheter linked to the needle or guide wire for deploying the needle or guidewire a precise distance radially from the distal portion.

32. The system of claim 24, wherein the catheter includes a deflecting element for directing the puncturing element substantially transversely with respect to the longitudinal axis when the puncturing element is deployed.

33. The system of claim 24, wherein the imaging element comprises an ultrasound transducer.

34. The system of claim 24, wherein the catheter includes a lumen extending from the proximal portion to the distal portion for receiving the imaging element therein.

35. The system of claim 24, wherein the drug delivery element comprises an indwelling catheter deployable in combination with the puncturing element to the target region.

36. The system of claim 24, wherein the drug delivery element comprises an infusion catheter.

37. The system of claim 24, wherein the drug delivery element comprises a perfusion balloon.

38. The system of claim 24, wherein the drug delivery element includes a first electrode thereon adapted to be electrically coupled to a second electrode, whereby when direct current is directed between the first and second electrodes, a substance from the drug delivery element is ionophoretically directed from the drug delivery element towards the second electrode.

39. The system of claim 24, wherein the imaging element comprises an ultrasound transducer.

40. The system of claim 39, wherein the ultrasound transducer is configured for imaging in an imaging plane substantially normal to the longitudinal axis of the catheter.

41. The system of claim 39, wherein the ultrasound transducer is insertable into a lumen of the catheter until it is disposed adjacent the orientation element.

* * * * *

UNITED STATES PATENT AND TRADEMARK OFFICE
CERTIFICATE OF CORRECTION

PATENT NO. : 6,283,951 B1
DATED : September 4, 2001
INVENTOR(S) : Flaherty et al.

It is certified that error appears in the above-identified patent and that said Letters Patent is hereby corrected as shown below:

Title page,
References Cited, U.S. PATENT DOCUMENTS,
For 5,693,029, please change "Leonhart" to -- Leonhardt --.
OTHER PUBLICATIONS,
For the "Y. Kobayashi et al." reference, please change "perivascular" to -- Perivascular --.

Column 5,
Line 3, please change "introducing" to -- introduced --.

Column 8,
Line 7, please change "FIG. 4 is a side view detail" to -- FIGS. 4A and 4B are side view details --.
Lines 15 and 18, please change "is another" to -- is a side view of another --.

Column 9,
Line 23, please change "63" to -- 63 --.
Line 24, please change "70" to -- 70 --.
Line 25, please change "40" to -- 40 --.
Line 27, please change "Nos.08/730," to -- Nos. 08/730, --.
Line 38, please change "lumen 36" to -- lumen 32 --.

Column 13,
Line 26, please change "2.14, that ay" to -- 214, that may --.

UNITED STATES PATENT AND TRADEMARK OFFICE
CERTIFICATE OF CORRECTION

PATENT NO. : 6,283,951 B1
DATED : September 4, 2001
INVENTOR(S) : Flaherty et al.

It is certified that error appears in the above-identified patent and that said Letters Patent is hereby corrected as shown below:

Column 16,
Line 11, please change "passage 23" to -- passage 223 --.

Signed and Sealed this

Fifth Day of November, 2002

*Attest:*

*Attesting Officer*

JAMES E. ROGAN
*Director of the United States Patent and Trademark Office*